US010119137B2

(12) United States Patent
Tran

(10) Patent No.: US 10,119,137 B2
(45) Date of Patent: Nov. 6, 2018

(54) METHODS USED TO TREAT CANCER

(71) Applicant: THE TRANSLATIONAL GENOMICS RESEARCH INSTITUTE, Phoenix, AZ (US)

(72) Inventor: Nhan Tran, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/204,969

(22) Filed: Jul. 7, 2016

(65) Prior Publication Data

US 2017/0009231 A1 Jan. 12, 2017

Related U.S. Application Data

(60) Provisional application No. 62/190,604, filed on Jul. 9, 2015.

(51) Int. Cl.
*A61K 48/00* (2006.01)
*C07H 21/02* (2006.01)
*C07H 21/04* (2006.01)
*C12N 15/11* (2006.01)
*C12N 15/113* (2010.01)
*A61K 31/7088* (2006.01)
*A61K 45/06* (2006.01)
*A61K 31/495* (2006.01)

(52) U.S. Cl.
CPC .......... *C12N 15/113* (2013.01); *A61K 31/495* (2013.01); *A61K 31/7088* (2013.01); *A61K 45/06* (2013.01); *C12N 15/1135* (2013.01); *C12N 2310/122* (2013.01); *C12N 2310/14* (2013.01); *C12N 2310/531* (2013.01); *C12N 2320/31* (2013.01); *C12N 2320/35* (2013.01)

(58) Field of Classification Search
USPC ............................................ 514/44; 536/24.5
See application file for complete search history.

(56) References Cited

PUBLICATIONS

Ensign et al. Jbc, 2013 vol. 288, No. 30:21887-21897.*
Kim et al. (Nucliec Acids Reseach, 2018 vol. 46:1424-1440).*
Jin et al. (Bioconjugate Chem., 2011 vol. 22:2568-2572).*
Yang et al. (Mol. Pharmaceutics, 2017 vol. 14:1012-1022).*
Kim et al. (Nucleic Acids Research, 2018 vol. 46:1424-1440).*
Fitzgibbons, et al. Prognostic Factors in Breast Cancer. Archives of Pathology & Laboratory Medicine, vol. 124, No. 1, 966-978, Jun. 2000.
Ross et al. The HER-2/neu Gene and Protein in Breast Cancer 2003: Biomarker and Target of Therapy. The Oncologist, 8:307-25, 2003.
Hanley, et al. The meaning and use of the area under a receiver operating characteristic (ROC) curve. Radiology, 143: 29-36 (1982).
Hoelzinger, et al. Gene expression profile of glioblastoma multiforme invasive phenotype points to new therapeutic targets. Neoplasia. 2005; 7:7-16.
Mariani, et al. Glioma cell motility is associated with reduced transcription of proapoptotic and proliferation genes: a cDNA microarray analysis. J Neuro-Oncol. 2001; 53:161-76.

(Continued)

*Primary Examiner* — Terra C Gibbs

(57) ABSTRACT

The invention encompasses methods used in the sensitization and treatment of cancer based upon the expression of SGEF.

13 Claims, 12 Drawing Sheets

Specification includes a Sequence Listing.

(56) References Cited

PUBLICATIONS

Tran, et al. The tumor necrosis factor-like weak inducer of apoptosis (TWEAK)-fibroblast growth factor-inducible 14 (Fn14) signaling system regulates glioma cell survival via NFkappaB pathway activation and BCL-XL/BCL-W expression. J Biol Chem. 2005; 280:3483-92.

Tran, et al. Increased fibroblast growth factor-inducible 14 expression levels promote glioma cell invasion via Rac1 and nuclear factor-kappaB and correlate with poor patient outcome. Cancer Res. 2006; 66:9535-42.

Munson, et al. Anti-invasive adjuvant therapy with imipramine blue enhances chemotherapeutic efficacy against glioma. Sci Transl Med. 2012; 4:127ra36.

Acharyya, et al. A CXCL1 Paracrine Network Links Cancer Chemoresistance and Metastasis. Cell. 2012; 150:165-78.

Han, et al. Exogenous IGFBP-2 promotes proliferation, invasion, and chemoresistance to temozolomide in glioma cells via the integrin beta1-ERK pathway. British journal of cancer 2014; 111:1400-9.

Hanahan, et al. Hallmarks of cancer: the next generation. Cell. 2011; 144:646-74.

Roos, et al. DNA damage-induced apoptosis: From specific DNA lesions to the DNA damage response and apoptosis. Cancer letters. 2012.

Zhang, et al. The role of the BRCA1 tumor suppressor in DNA double-strand break repair. Molecular cancer research : MCR. 2005; 3:531-9.

Lukas, et al. More than just a focus: The chromatin response to DNA damage and its role in genome integrity maintenance. Nature cell biology. 2011; 13:1161-9.

Fortin, et al. Tumor necrosis factor-like weak inducer of apoptosis stimulation of glioma cell survival is dependent on Akt2 function. Mol Cancer Res. 2009; 7:1871-81.

Fortin, et al. The Src homology 3 domain-containing guanine nucleotide exchange factor is overexpressed in high-grade gliomas and promotes tumor necrosis factor-like weak inducer of apoptosis-fibroblast growth factor-inducible 14-induced cell migration and invasion via tumor necrosis factor receptor-associated factor 2. The Journal of biological chemistry. 2013; 288:21887-97.

Tran, et al. The human Fn14 receptor gene is up-regulated in migrating glioma cells in vitro and overexpressed in advanced glial tumors. Am J Pathol. 2003; 162:1313-21.

Franken, et al. Clonogenic assay of cells in vitro. Nat Protoc. 2006; 1:2315-9.

Kwiatkowska, et al. The small GTPase RhoG mediates glioblastoma cell invasion. Molecular cancer. 2012; 11:65.

Garcia-Mata, et al. Analysis of activated GAPs and GEFs in cell lysates. Methods in Enzymology. 2006; 406:425-37.

Guilluy, et al. Analysis of RhoA and Rho GEF activity in whole cells and the cell nucleus. Nature protocols. 2011; 6:2050-60.

Salhia' et al.The guanine nucleotide exchange factors trio, Ect2, and Vav3 mediate the invasive behavior of Glioblastoma. The American journal of pathology. 2008; 173:1828-38.

REpository for Molecular BRAin Neoplasia DaTa (Rembrandt) database (National Cancer Institute. 2005. Rembrandt home page. http://rembrandt.nci.nih.gov. Accessed Nov. 26, 2012).

Nessa P., (2012) Pearson Correlation (v1.0.6) in Free Statistics Software (v1.1.2347), Office for Research Development and Education, URL http://www.wessa.net/rwasp_correlation.wasp/.

Robe, et al. In vitro and in vivo activity of the nuclear factor-kappaB inhibitor sulfasalazine in human glioblastomas. Clin Cancer Res. 2004; 10:5595-603.

Kuo, et al. Gamma-H2AX—a novel biomarker for DNA double-strand breaks. In Vivo. 2008; 22:305-9.

Ql, et al. Isolation of the novel human guanine nucleotide exchange factor Src homology 3 domain-containing guanine nucleotide exchange factor (SGEF) and of C-terminal SGEF, an N-terminally truncated form of SGEF, the expression of which is regulated by androgen in prostate cancer cells. Endocrinology. 2003; 144:1742-52.

Krishna Subbaiah, et al. The invasive capacity of HPV transformed cells requires the hDlg-dependent enhancement of SGEF/RhoG activity. PLoS Pathog. 2012;8:e1002543.

Gerloff, et al. BRCT domains: A little more than kin, and less than kind. FEBS Lett. 2012; 586:2711-6.

Raychaudhuri, et al. Aberrant constitutive activation of nuclear factor kappaB in glioblastoma multiforme drives invasive phenotype. Journal of neuro-oncology. 2007; 85:39-47.

Conti, et al. Expression of the tumor necrosis factor receptor-associated factors 1 and 2 and regulation of the nuclear factor-kappaB antiapoptotic activity in human gliomas. Journal of neurosurgery. 2005; 103:873-81.

Ding, et al. Radiosensitization by inhibition of IkappaB-alpha phosphorylation in human glioma cells. Radiat Res. 2003; 160:232-7.

Bredel, et al. Tumor necrosis factor-alpha-induced protein 3 as a putative regulator of nuclear factor-kappaB-mediated resistance to 06-alkylating agents in human glioblastomas. Journal of clinical oncology: official journal of the American Society of Clinical Oncology. 2006; 24:274-87.

Brown, et al. The Fn14 cytoplasmic tail binds tumour-necrosis-factor-receptor-associated factors 1, 2, 3 and 5 and mediates nuclear factor-kappaB activation. Biochem J. 2003; 371:395-403.

Patel, et al. Differential activation and function of Rho GTPases during Salmonella-host cell interactions. J Cell Biol. 2006; 175:453-63.

Ellerbroek, et al. SGEF, a RhoG guanine nucleotide exchange factor that stimulates macropinocytosis. Molecular biology of the cell. 2004; 15:3309-19.

Williams Carol L The polybasic region of Ras and Rho family small GTPases: a regulator of protein interactions and membrane association and a site of nuclear localization signal sequences. Cellular signalling. 2003; 15:1071-80.

Johannessen, et al. Molecular mechanisms of temozolomide resistance in glioblastoma multiforme. Expert review of anticancer therapy. 2012; 12:635-42.

Quiros, et al. Rad51 and BRCA2—New molecular targets for sensitizing glioma cells to alkylating anticancer drugs. PloS one. 2011;6:e27183.

Kitange, et al. Inhibition of histone deacetylation potentiates the evolution of acquired temozolomide resistance inked to MGMT upregulation in glioblastoma xenografts. Clin Cancer Res. 2012; 18:4070-9.

Zhai, et al.Radiation enhances the invasive potential of primary glioblastoma cells via activation of the Rho signaling pathway. Journal of neuro-oncology. 2006; 76:227-37.

Monferran, et al. Alphavbeta3 and alphavbeta5 integrins control glioma cell response to ionising radiation through ILK and RhoB. International journal of cancer Journal international du cancer 2008; 123:357-64.

Giavazzi, et al. Metastatic behavior of an adriamycin-resistant murine tumor. Cancer research. 1983; 43:5081-6.

Liang, et al. Selection with melphalan or paclitaxel (Taxol) yields variants with different patterns of multidrug resistance, integrin expression and in vitro invasiveness. Eur J Cancer. 2001; 37:1041-52.

Glynn, et al. A new superinvasive in vitro phenotype induced by selection of human breast carcinoma cells with the ahemotherapeutic drugs paclitaxel and doxorubicin. British journal of cancer. 2004; 91:1800-7.

Alexander, et al. Cancer invasion and resistance: interconnected processes of disease progression and therapy failure. Trends Mol Med. 2012; 18:13-26.

Tait, et al. Survival of patients with glioblastoma multiforme has not improved between 1993 and 2004: analysis of 625 cases. Br J Neurosurg. 2007; 21:496-500.

Barnholtz-Sloan, et al. Relative survival rates and patterns of diagnosis analyzed by time period for individuals with primary malignant brain tumor, 1973-1997. Journal of neurosurgery. 2003; 99:458-66.

(56) References Cited

OTHER PUBLICATIONS

Barazzuol, et al. Evaluation of poly (ADP-ribose) polymerase inhibitor ABT-888 combined with radiotherapy and temozolomide in glioblastoma. Radiat Oncol. 2013; 8:65.

McEllin, et al. PTEN loss compromises homologous recombination repair in astrocytes: implications for glioblastoma herapy with temozolomide or poly(ADP-ribose) polymerase inhibitors. Cancer research. 2010; 70:5457-64.

Russo, et al. In vitro and in vivo radiosensitization of glioblastoma cells by the poly (ADP-ribose) polymerase inhibitor E7016. Clin Cancer Res. 2009; 15:607-12.

Nadkarni, et al. Atm inhibitor Ku-55933 increases the Tmz responsiveness of only inherently Tmz sensitive Gbm mils_ Journal of neuro-oncology. 2012; 110:349-57_.

Ho, et al. RhoJ regulates melanoma chemoresistance by suppressing pathways that sense Dna damage. Cancer esearch. 2012; 72:5516-28_.

\* cited by examiner

METHODS USED TO TREAT CANCER

CROSS-REFERENCE TO RELATED APPLICATION

The present application claims the benefit of U.S. Provisional Application No. 62/190,604 filed Jul. 9, 2015, the contents of which are incorporated herein by reference for any purpose.

BACKGROUND OF THE INVENTION

Glioblastoma (GB) is the most common form of primary adult brain tumors characterized by a poorly defined tumor mass resulting from highly invasive cells. The problem of resistance to the standard anti-proliferative treatment of concomitant radiotherapy with chemotherapy using the alkylating agent temozolomide (TMZ) is common, and actively invading cells survive the current therapeutic regimens. Glioma cells with the increased capacity for migration have a decreased expression of pro-apoptotic genes and are less sensitive to cytotoxic therapy-induced apoptosis (1-4); the knockdown of several pro-invasive gene candidates in GB decreases glioma cell migration rate and subsequently sensitizes the cells to cytotoxic therapy and importantly, therapy directed at mediators of invasion has been shown to increase chemotherapeutic sensitivity (5-7).

An increased capacity for cell survival results from the multi-faceted regulation of pathways involved in promoting cell growth, replication and spread, and preventing apoptosis in response to cytotoxic insult (8). Treatment strategies of tumor irradiation and temozolomide administration in glioblastoma lead to the formation of DNA double strand breaks (DSBs), either directly, or via mismatch repair conversion of O(6)-methylguanine adducts into DSBs, respectively (9). DSBs are primarily repaired through two mechanisms, homologous recombination (HR) and non-homologous end-joining (NHEJ). HR repair makes use of a non-damaged homologous DNA template, and thus is characterized as an error free mechanism, while NHEJ has no homologous strand for template use resulting in sequence errors near the break point (10).

DNA repair is initiated via sensing of DSBs by three kinases: ataxia telangiectasia mutated (ATM), ataxia telangiectasia and Rad3 related (ATR), and Chk2. Subsequently, the early phosphorylation of histone H2A.X ($\gamma$H2A.X) by ATM occurs at damaged DNA foci and leads to the phosphorylation of mediator of DNA damage checkpoint protein 1 (MDC1), with subsequent chromatin remodeling and recruitment of DNA repair proteins (11). BRCA1 is one such key mediator of HR and NHEJ repair; after exposure to DNA damaging agents BRCA1 is rapidly phosphorylated by ATM, ATR, and Chk2, and relocated to sites of replication forks with $\gamma$H2A.X foci, where it recruits further proteins including BRCA2 and Rad51 to mediate strand exchange toward DNA repair and cell survival (10).

One key driver in GB that has been characterized to promote both cell invasion and cell survival is the transmembrane receptor fibroblast growth factor inducible-14 (Fn14). Fn14 is a member of the tumor necrosis factor receptor superfamily with one known ligand, the tumor necrosis factor-like weak inducer of apoptosis (TWEAK). Signaling through Fn14 by its cytokine ligand TWEAK activates Rac1, Akt, and NF-$\kappa$B-pathways, and has been shown to promote increased cell invasion and resistance to cytotoxic therapy-induced apoptosis (3, 4, 12).

As such, there is a demonstrated need to further investigate in GB systems molecules that not only promote GB's survival during chemotherapy treatment, but is also itself an attractive target for therapeutic targeting.

BRIEF SUMMARY OF THE INVENTION

Embodiments of the invention include a method of sensitizing a patient with cancer to a therapeutic treatment by administering a src-homology 3 domain containing guanine nucleotide exchange factor (SGEF) inhibitor. The inhibition of SGEF may sensitize the cancer to the therapeutic treatment. The inhibitor of SGEF may include a small hairpin RNA which targets the nucleic acid encoding for SGEF. The cancer may be glioblastoma, such as invasive glioblastoma. The SGEF inhibitor may convert the invasive glioblastoma to a non-migratory phenotype. In some aspects, after sensitization, the patient may be treated with a therapeutically effective amount of the therapeutic treatment. The therapeutic treatment may comprise of the administration of one or more of the following compounds: TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab.

Some embodiments of the invention may also include a method of treating a patient with invasive glioblastoma. The method may include sensitizing the patient by reducing the expression of SGEF and then by administering a therapeutically effective amount of a treatment to the patient. The treatment may comprise of the administration of one or more of the following compounds: TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab. Reducing the expression of SGEF by an inhibitor may be achieved by using an SGEF inhibitor which can be a small hairpin RNA which targets the nucleic acid encoding for SGEF. The SGEF inhibitor may convert the invasive glioblastoma to a non-migratory phenotype. In some aspects, the treatment may comprise of the administration of a therapeutically effective amount of temozolomide and/or radiation.

Further embodiments of the invention may include a method of sensitizing a patient with cancer to a therapeutic treatment by administering to the patient a breast cancer type 1 susceptibility gene (BRCA1) inhibitor. The BRCA1 inhibitor can sensitize the cancer to a therapeutic treatment. The inhibitor of BRCA1 may be a small interfering RNA which targets the nucleic acid encoding for BRCA1. The cancer may be glioblastoma. The glioblastoma may be invasive. The BRCA1 inhibitor may convert the invasive glioblastoma to a non-migratory phenotype. In some aspects, the patient may be administered a therapeutically effective amount of the therapeutic treatment, which may be selected from the group consisting of: TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab.

BRIEF DESCRIPTION OF THE FIGURES

A more complete understanding of the present invention may be derived by referring to the detailed description when considered in connection with the following illustrative figures.

Figure 1:
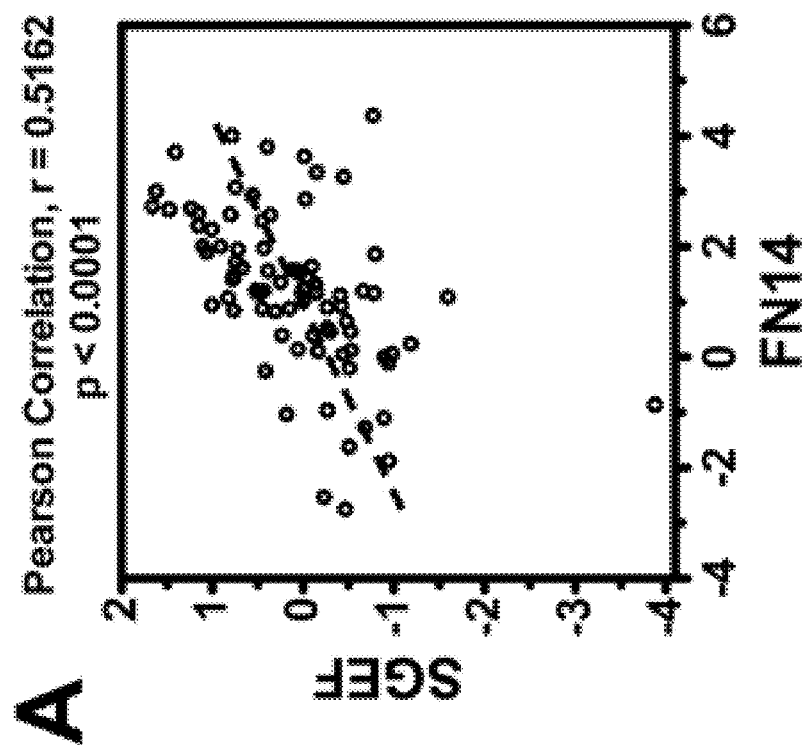
FIG. 1. SGEF mRNA and protein expression is inducible via TWEAK cytokine stimulation. (A) SGEF and Fn14 (Only receptor for TWEAK cytokine) mRNA expression from the publicly available REMBRANDT dataset of 82 GB tumors was accessed and assessed using the Pearson product moment correlation statistic ($p<0.001$). (B & C) T98G and U118 glioma cells were cultured in reduced serum (0.5% FBS DMEM) for 16 hours prior to stimulation with TWEAK (100 ng/mL) for the indicated times. SGEF mRNA (B) and protein (C) expression were analyzed via qPCR with fold change relative to histone and via western blotting with the indicated antibodies, respectively.
Figure 1:
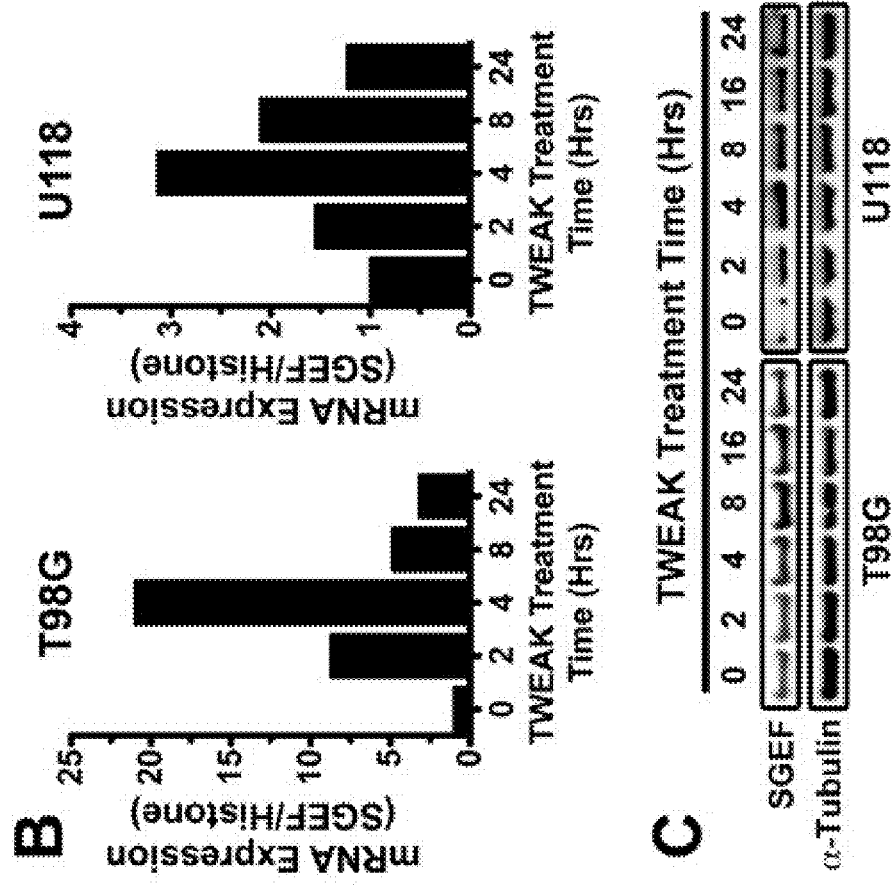

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Gliomas, primary brain tumors that derive from glial support cells, are the most common primary tumor of the adult central nervous system and will result in an estimated 13,000 deaths in 2010. Adult gliomas of astrocytic origin (astrocytomas) comprise a spectrum of neoplasms that are generally classified by WHO standards into low-grade benign tumors (i.e. juvenile pilocytic astrocytoma, diffuse astrocytoma) and high-grade malignant tumors (i.e. anaplastic astrocytoma and glioblastoma multiforme; GBM). Patients diagnosed with grade IV GBM, the most aggressive malignant glioma, have a median survival of 9-12 months after the onset of clinical symptoms. Molecular analyses of glioma specimens have identified several common genetic alterations (e.g., p16INK4a deletion) and gene expression changes (e.g., EGFR overexpression) that may contribute to glioblastoma formation.

In general, gliomas are extremely difficult to treat using conventional approaches. This is primarily due to the intrinsic propensity of glioma cells to exit the tumor core and invade the adjacent normal brain parenchyma. These migrating cells escape surgical resection and are poorly targeted by radiation or chemotherapy. They sometimes travel over long distances, frequently along blood vessel and fiber tracts, and then initiate secondary tumor growth at their final destination. This distinguishing invasive ability is not shared by nonglial cells that metastasize from other primary tumor sites (e.g. breast) to brain tissue. The invasion of glioma cells is likely triggered by a presently undefined signal or signals that promote a cascade of cellular responses, including cell elongation, integrin-mediated cell attachment to extracellular matrix (ECM) molecules, the production and secretion of ECM-degrading enzymes, and cell movement.

Migrating glioma cells exhibit decreased susceptibility to pro-apoptotic agents, providing them with an additional mechanism for resisting current radiological and chemotherapeutic treatment modalities.

Herein, the inventor demonstrates that SGEF and BRCA1 serve as therapeutic targets to treat glioblastoma. Inhibition of SGEF or BRCA1 sensitizes cancer cells to temozolimide and other conventional treatments as SGEF and BRCA1 are crucial proteins of pathways that contribute to glioma cell migration and invasion.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moeties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, differential methylation, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay. Methods of detecting expression may include methods of purifying nucleic acid, protein, or some other material depending on the type of marker. Any method of nucleic acid purification may be used, depending on the type of marker. Examples include phenol alcohol extraction, ethanol extraction, guanidium isothionate extraction, gel purification, size exclusion chromatography, cesium chloride preparations, and silica resin preparation. Any method of protein purification may be used, also depending on the type of marker. Examples include size exclusion chromatography, hydrophobic interaction chromatography, ion exchange chromatography, affinity chromatograpy (including affinity chromatography of tagged proteins), metal binding, immunoaffinity chromatography, and HPLC.

Nucleic acid amplification is a process by which copies of a nucleic acid may be made from a source nucleic acid. Nucleic acids that may be subjected to amplification may be from any source. In some nucleic amplification methods, the copies are generated exponentially. Examples of nucleic acid amplification include but are not limited to: the polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as Φ29, whole genome PCR, in vitro transcription with any RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that is selected based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. Often, the result of a real-time PCR will be expressed in the terms of cycle threshold (Ct) values. The Ct represents the number of PCR cycles for the fluorescent signal from a real-time PCR reaction to cross a threshold value of fluorescence. Ct is inversely proportional to the amount of target nucleic acid originally present in the sample. RNA may be detected by PCR analysis by creating a DNA template from RNA through a reverse transcriptase enzyme.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)$_2$, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent), stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an IHC assay configured to detect a marker, differential detection of bound RNA on a microarray to which a sequence capable of binding to the marker is bound, differential results in measuring RTPCR measured in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, 100,000×, 10,000×, 1000×, 100×, 10×, 5×, 2×, 1×, 0.5×, 0.1×0.01×, 0.001×, 0.0001×, 0.00001×, 0.000001×, 0.0000001× or less than that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies particular physiological or cellular characteristics. In diagnosing the presence of a disease, a threshold value may be obtained by performing the assay method on samples obtained from a population of patients having a certain type of disease (cancer for example), and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that signify a particular physiological or cellular characteristic. For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982).

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up. A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups. A value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer. Methods of identifying subjects suspected of having cancer include but are not limited to: physical examination, family medical history, subject medical history including exposure to environmental factors, biopsy, or any of a number of imaging technologies such as ultrasonography, computed tomography, magnetic resonance imaging, magnetic resonance spectroscopy, or positron emission tomography.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

A specific nucleic acid may include a label. A label may be any substance capable of aiding a machine, detector, sensor, device, or enhanced or unenhanced human eye from differentiating a sample that displays positive expression from a sample that displays reduced expression. Examples of labels include but are not limited to: a radioactive isotope or chelate thereof, a dye (fluorescent or nonfluorescent), stain, enzyme, or nonradioactive metal. Specific examples include but are not limited to: fluorescein, biotin, digoxigenin, alkaline phosphatase, biotin, streptavidin, $^{3}H$, $^{14}C$, $^{32}P$, $^{35}S$, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

An oligonucleotide used to detect to an allele may be affixed to a solid substrate. Alternatively, the sample may be affixed to a solid substrate and the nucleic acid reagent placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the cases of a Southern Blot, Northern blot or other method that affixes the sample to a substrate.

Specific antibodies, buffers, and other reagents may be configured to detect binding of the antibody to the specific epitope. One or more of the antibodies may be labeled with a fluorescent, enzymatic, magnetic, metallic, chemical, or other label that signifies and/or locates the presence of specifically bound antibody. Secondary antibodies may specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody.

The invention further encompasses pharmaceutical compositions that are known to target SGEF and BRCA1 and inhibit expression, functionality, disrupt interactions with other proteins on the cell mobility/invasive pathway, and other methods that may otherwise inhibit SGEF and BRCA1. Such pharmaceutical compositions may take any physical form necessary depending on a number of factors including the desired method of administration and the physicochemical and stereochemical form taken by the disclosed substances or pharmaceutically acceptable salts of the compound. Such physical forms include a solid, liquid, gas, sol, gel, aerosol, or any other physical form now known or yet to be disclosed. Pharmaceutical compositions may be prepared using methodology well known in the pharmaceutical art. A pharmaceutical composition may include a second effective compound of a distinct chemical formula. This second effective compound may have the same or a similar molecular target as the target or it may act upstream or downstream of the molecular target with regard to one or more biochemical pathways.

Pharmaceutical compositions include materials capable of modifying the physical form of a dosage unit. In one nonlimiting example, the composition includes a material that forms a coating that holds in the compound. Materials that may be used in such a coating, include, for example, sugar, shellac, gelatin, or any other inert coating agent.

Pharmaceutical compositions may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or tri-phasic systems.

The pharmaceutical composition may include the form of a solvate. Such solvates are produced by the dissolution of the disclosed compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the compound to treat the affliction without serious complications arising from the use of the solvent in a majority of patients.

Pharmaceutical compositions may also include a pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. Treatment may be delivered in the context of a vesicle such as a liposome or any other natural or synthetic vesicle.

A pharmaceutical composition formulated so as to be administered by injection may be prepared by dissolving the compound with water so as to form a solution. In addition, a surfactant may be added to facilitate the formation of a homogeneous solution or suspension. Surfactants include any complex capable of non-covalent interaction with the substance so as to facilitate dissolution or homogeneous suspension of the compound.

Pharmaceutical compositions may be prepared in a form that facilitates topical or transdermal administration. Such preparations may be in the form of a liquid solution, cream, paste, lotion, shake lotion, powder, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to affect a particular purpose as well as a pharmacologically acceptable dose determined by toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed substance for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ (the half maximal inhibitory concentration) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized.

The effective amount of the disclosed substance to results in the slowing of expansion of the cancer cells would preferably result in a concentration at or near the target tissue that is effective in slowing cellular expansion in cancer cells, but have minimal effects on non-cancer cells, including non-cancer cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed substance(s) encompasses any method of dosing of a compound. Dosing of the disclosed substance may include single or multiple administrations of any of a number of pharmaceutical compositions. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions may be administered prior to, concurrently with, or after administration of a second pharmaceutical composition. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

Pharmaceutical compositions may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to cancer, in particular, where non- or precancerous cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-90, incorporated by reference). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. Further examples include leukoplakia, featuring a benign-appearing hyperplastic or dysplastic lesion of the epithelium, or Bowen's disease, a carcinoma in situ. Both of theses are pre-cancerous lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the therapeutic treatment compound may be determined by one or more physical factors such as tumor size and grade or one or more molecular markers and/or expression signatures that indicate prognosis and the likely response to treatment. For example, determination of estrogen (ER) and progesterone (PR) steroid hormone receptor status has become a routine procedure in assessment of breast cancer patients. See, for example, Fitzgibbons et al, Arch. Pathol. Lab. Med. 124: 966-78, 2000, incorporated by reference. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition. Such predisposing factors include but are not limited to chromosomal translocations associated with a malignancy such as the Philadelphia chromosome for chronic myelogenous leukemia and t(14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition is administered in combination with a therapeutically effective amount of radiotherapy. The radiotherapy may be administered concurrently with, prior to, or following the administration of the pharmaceutical composition. The radiotherapy may act additively or synergistically with the pharmaceutical composition. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination may include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition are hematopoietic colony stimulating factors. Examples of hematopoietic colony stimulating factors include, but are not limited to, filgrastim, sargramostim, molgramostim and epoietin alfa. Alternatively, the pharmaceutical composition may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions may include analgesic agents. Such agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition may then be administered to the patient prior to restoring the entity's bone marrow by addition of either the patient's own or donor stem cells.

Cancers that may be treated by pharmaceutical compositions either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

The invention encompasses inhibitors of cell migration activity and inhibitors of effector recruitment activity. Inhibition encompasses any action that hinders, from any detectable level up to and including complete inactivation, the progression of a biological process. Such biological processes include expression of a gene or activities of a gene product, progression of a disease, normal and abnormal metabolic activities, interactions between entities within an organism, or interactions between one organism and another. Further nonlimiting examples of biological processes include development, death, maturation, infection, pain, apoptosis, or homeostasis. Inhibition includes actions that silence or repress the expression of a gene. Inhibition also includes actions that hinder the activity of the RNA product, protein product, or postranslationally modified protein product of a gene. Inhibition may be effectuated through a single agent that inactivates a single gene or gene product, by a single agent that inactivates a combination of more than one gene or gene product, a combination of agents that inactivates a single gene or gene product or a combination of agents that inactivates a combination of more than one gene or gene product.

Inhibition may be effectuated directly by an agent that directly causes the inhibition of a biological process or by agents that trigger one or more different biological processes to effectuate the inhibition of the first biological process. Agents that cause inhibition may also be called inhibitors. Examples of inhibitors include compositions such as compounds that trigger RNAi silencing such as microRNA or siRNA, small molecular compounds, proteins such as soluble receptors or antibodies or any fragment thereof, including an Fab, $F(ab)_2$, Fv, scFv, Fc, phage display antibody, peptibody or any other composition of matter that may inactivate or hinder a biological process. Further nonlimiting examples of inhibitors include X-rays, UV rays, visible light including laser light, and sound.

Cell migration activity includes any mode through which a cell may move in two-dimensional or three-dimensional space. Such migration includes movement through the use of pseudopodia including the adhesion of pseudopodia to a surface, a flagellum, a cilium, acts of amoeboid movement, extravasation, myosin-actin interactions, microtubule extension, or any other process through which a cell moves itself from one place to another or changes its morphology. In one aspect of the invention, cell migration activity is measured through cell adhesion. Using adhesion, cell migration activity may be measured by cell-cell aggregation, monolayer radial migration, including adhesion to a cell matrix comprising laminin, BSA or any other cell matrix component, three dimensional spheroid dispersion, or any other method that measures adhesion based cellular migration in space. Migration activity may be measured by any method that detects that a cell has moved from one place to another or has changed its morphology. Such methods include flow cytometry, capillary electrophoresis, visual examination by light, fluorescence, or electron microscopy, or any such method known in the art or yet to be developed. Inhibitors of cell migration activity are agents that disrupt any molecular or cellular process involved in cell migration activity.

Effector recruitment activity includes any activity of a protein that contributes to the formation of a complex of two or more molecules that serves to catalyze one or more chemical reactions. Effectors include any protein, nucleic acid or other molecule that may be included in a complex that performs one or more biological activities. Recruitment activity encompasses any protein-protein interaction including phosphorylation, dephosphorylation and other enzymatic activities, adhesion, signaling cascades, and cytokine/chemokine interactions, any protein-nucleic acid interactions, such as any of those involved in transcription, translation or DNA replication, or any other process that includes a protein interacting with another molecule. Inhibitors of effector recruitment activity may disrupt the interaction of a molecule with any of the proteins listed above, the interaction between any of those proteins with each other, and further includes any members of a complex that might be later identified.

In one aspect of the invention, inhibitors of effector recruitment activity may be identified on the basis of their ability to disrupt the binding of a molecule to one or more of its effectors. This specific binding may be measured by any method that allows the measurement of a protein-protein interaction known in the art. Such method include the following examples, alone or in combination as necessary: co-immunoprecipitation, biomolecular fluorescence complementation, fluorescence resonance energy transfer, label transfer, a yeast two-hybrid screen, in-vivo crosslinking, tandem affinity purification, chemical crosslinking, quantitative immunoprecipitation combined with knockdown (QUICK), dual polarization interferometry, protein-protein docking, static light scattering, immunoprecipitation plus mass-spectrometry, Strep-protein interaction experiment (SPINE), surface plasmon resonance, fluorescence correlation spectroscopy, or any other method of measuring the specific interaction between one protein and another now known in the art or yet to be disclosed.

In another aspect of the invention a glioblastoma patient is treated by first assessing the expression of a target and then treating with an effective dose of an inhibitor of that target, potentially in combination with Temozolimide. The effective dose of a compound is that amount effective to prevent occurrence of the symptoms of a disorder or to treat some symptoms of the disorder from which the patient suffers. Effective dose also includes an effective amount, a therapeutic amount, or any amount sufficient to elicit the desired pharmacological or therapeutic effects, thus resulting in effective prevention or treatment of the disorder. Thus, when treating a patient with glioblastoma, an effective amount of compound is an amount sufficient to slow, or arrest the progression, migration, metastasis, growth, or development of the tumor with the result that life is extended. Prevention includes a delay in onset of symptoms. Treatment includes a decrease in the symptoms associated with the disorder or an amelioration of the recurrence of the symptoms of the disorder. A pharmacologically acceptable dose encompasses any dose that may be administered to a patient that will not be lethal to the patient or cause effects that threaten the health or the life of the patient.

Patients include any human being, nonhuman primate, companion animal, or mammal suffering from a disease. In one aspect of the invention, the patient has symptoms that signify the presence of a tumor or other growth in the brain. Such symptoms include headache, seizures, mental or personality changes, mass effect, or one of a number of focal or localized systems including ringing or buzzing sounds, hearing loss, loss of coordination, reduced sensation, weakness or paralysis, difficulty with walking or speech, difficulty keeping balance, decreased muscle control, or double vision. Patients may display one or more different brain tumor types including acoustic neurinoma, astrocytoma, ependyoma, glioblastoma multiforme, meningioma, metastatic tumors originating from another tumor type, mixed glioblastoma, oligodendroglioblastoma, or pineal region tumor.

Examples

Elements and acts in the example are intended to illustrate the invention for the sake of simplicity and have not necessarily been rendered according to any particular sequence or embodiment. The example is also intended to establish possession of the invention by the Inventors.

Materials and Methods

Cell Culture Conditions.

Human astrocytoma cell lines U87, U118, and T98G (American Type Culture Collection), as well as primary glioblastoma xenograft cells (GBM & GBM TMZ-R lines) were maintained in DMEM (Gibco, USA) supplemented with 10% heat-inactivated fetal bovine serum (FBS; Gibco, USA) at 37° C. with 5% $CO_2$. For all assays with TWEAK treatment, cells were cultured in reduced serum (0.5% fetal bovine serum) for 16 h before stimulation with recombinant TWEAK at 100 ng/mL in DMEM+0.1% bovine serum albumin for the indicated times.

Antibodies, Plasmids, Reagents, and Western Blot Analysis.

A polyclonal SGEF antibody was purchased from Sigma (St. Louis, Mo.). A monoclonal tubulin antibody was purchased from Millipore (Billerica, Mass.). A polyclonal antibody for phospho-BRCA1 (Ser1524), and monoclonal antibodies for BRCA1, cleaved PARP, phospho-Histone H2A.X (Ser139), Histone H2A.X, Histone H3, and NF-κB p65 were purchased from Cell Signaling Technologies (Beverly, Mass.). Lipofectamine RNAiMax was purchased from Invitrogen. Human recombinant TWEAK was purchased from PeproTech (Rock Hill, N.J.). Human placental laminin and temozolomide were obtained from Sigma. In certain experiments cells were pre-incubated for 1 h with either 50 μM SN50 or SN50M (Calbiochem) prior to TWEAK addition. Or, in certain experiments glioma cells were transiently transfected with either control or IκBαM super-repressor expressing plasmids (Addgene, Cambridge, Mass.) using the Effectene transfection protocol (Qiagen, Valencia, Calif.) for 24 h prior to culture in reduced serum medium (0.5% FBS DMEM) for 16 h with subsequent addition of TWEAK for 4 h. Plasmids: pGEX4T-1-RhoG(15A) was obtained from Dr. Keith Burridge (U. North Carolina-Chapel Hill).

For immunoblotting, cells were lysed in 2×SDS sample buffer (0.25 M Tris-HCl, pH 6.8, 10% SDS, 25% glycerol) containing 10 μg/mL aprotinin, 10 μg/mL leupeptin, 20 mM NaF, 2 mM sodium orthovanadate, and 1 mM phenylmethylsulfonyl fluoride. Protein concentrations were determined using the BCA assay (Pierce) with bovine serum albumin as a standard. Thirty micrograms of total protein were loaded per lane and separated by SDS PAGE. After 4° C. transfer, the nitrocellulose (Invitrogen) was blocked with either 5% nonfat milk or 5% BSA in Tris-buffered saline, pH 8.0, containing 0.1% Tween 20 (TBST) prior to addition of primary antibodies and followed with peroxidase-conjugated anti-mouse IgG or anti-rabbit IgG. Protein was detected using SuperSignal West Dura Chemiluminescent Substrate (Thermo Scientific) with a UVP BioSpectrum 500 Imaging System (Upland, Calif.). Densitometry was calculated via Image J software.

RNA Isolation and Quantitative Reverse Transcriptase-Polymerase Chain Reaction (qRT-PCR).

Total RNA was isolated as previously described (1). cDNA was synthesized from 500 ng of total RNA in a 20 μL reaction volume using the SuperScript III First-Strand Synthesis SuperMix Kit (Invitrogen) for 50 minutes at 50° C., followed by 85° C. for 5 minutes. qPCR analysis of SGEF (sense: 5'-TGC TGA AAG GAC AAG GAA CA-3' (SEQ ID NO:1); anti-sense: 5'-GTA GTT TTG ATA CAG GAC AGC ATT-3'(SEQ ID NO:2)) and histone H3.3 (sense: 5'-CCA CTG AAC TTC TGA TTC GC-3'(SEQ ID NO:3); anti-sense: 5'-GCG TGC TAG CTG GAT GTC TT-3'(SEQ ID NO:4)) mRNA levels was conducted using SYBR green (Roche) fluorescence for detection of amplification after each cycle with LightCycler analysis software and quantified as previously described (14).

Biotinylated Electrophoretic Mobility Shift Assay.

T98G glioma cells were plated at a density of $3 \times 10^6$ in 100 $mm^2$ tissue culture dishes in normal growth medium. After 12 h, cells were cultured under reduced serum (0.5% FBS) for an additional 16 h before TWEAK (100 ng/mL) addition for 2 h. Isolation of cell nuclear protein was carried out using the NE-PER kit (Pierce) according to the protocol of the manufacturer. Protein-DNA complexes were detected using biotin end-labeled double-stranded DNA 23-mer probes containing the NF-κB binding sites within the SGEF promoter (NF-κB-SGEF wt target sequence: 5'-GTC TAG GAG GCA AAT CCC AGA AA-3' (SEQ ID NO:5); NF-κB-SGEF mt target sequence: 5'-GTC TAG GAG CCA GAT CGC AGA AA-3'(SEQ ID NO:6)). The binding reactions were done using the LightShift kit (Pierce) according to the protocol of the manufacturer. Where indicated, 200-fold molar excess of unlabeled NF-κB-SGEF wt oligonucleotides or anti-p65 antibody was included. The reaction products were resolved by gel electrophoresis and detected by chemiluminescence according to the protocol of the manufacturer (Pierce).

Lentiviral Production.

Lentiviral vectors containing shRNA targeting SGEF (shSGEF-12 & shSGEF-13) or control empty vector (control) were obtained from Open Biosystems (Fisher Scientific, Pittsburgh, Pa.) and packaged for lentiviral production as previously described (13). Clonogenic and apoptosis studies.

Observations of colony forming capacity following cytotoxic insult were performed as described (15). Briefly, T98G, U87 and U118 cells stably expressing either control or shRNA targeting SGEF were treated with the indicated concentrations of TMZ. In certain experiments cells were additionally transfected with siRNA targeting control luciferase or BRCA1 for 72 h prior to the addition of TMZ. Cells were trypsinized 24 h post-TMZ treatment and plated in triplicate in 6-well cell culture dishes at 250 cells per well. Colonies were allowed to grow until controls reached a 50 cell density (approximately 6-7 days) before being fixed briefly in a 10% (v/v) methanol 10% (v/v) glacial acetic acid solution, stained with a 0.5% (w/v) crystal violet solution and washed with de-ionized water. Apparent colonies were recorded, and surviving fractions were determined relative to the non-treated control for each cell line.

For apoptotic studies, T98G and U87 control or shSGEF cells were treated with TMZ (500 μM) for 48 h and whole cell lysates were analyzed for cleaved PARP by western blot. Alternatively, glioma cells were plated onto 10-well slides pre-coated with 10 ug/mL laminin. After 24 h cells were treated with TMZ (500 μM) for an additional 48 h. Cells were fixed with 4% paraformaldehyde, stained with Pro-Long Gold Antifade Reagent with DAPI (Molecular Probes) and evaluated by nuclear morphology. Cells with condensed, fragmented chromatin were manually scored as apoptotic cells. At least three fields were evaluated per well, and data reported as apoptotic cells/total cells×100.

Nucleotide-Free GEF Pulldowns.

RhoG activity was measured as previously described using a GST-ELMO-NT fusion protein (16). Affinity pulldowns of active SGEF bound to RhoG were performed using a nucleotide free RhoG mutant (G15A) expressed and purified as described (17). Recombinant RhoG G15A-GST protein and GST-ELMO-NT were produced in *Escherichia coli* (BL21) cells. Cells were lysed in B-PER lysis buffer (Pierce) containing protease inhibitors, and purified with glutathione sepharose beads (GE Healthcare).

Isolation of cell nuclear protein was performed according to Guilluy et al (18). Briefly, $10^7$ U87 cells were grown in 10 cm dishes before treatment with TMZ (500 µM) for the indicated times. Cells were washed in ice-cold PBS containing protease inhibitors and lysed in a 1 mL hypotonic solution (10 mM HEPES (pH 7.9), 1.5 mM $MgCl_2$, 10 mM KCl and 0.5 mM DTT (freshly added before use)). Lysates were homogenized and centrifuged at ~300 g for 5 minutes at 4° C. Pellets were washed twice in 1.5 mL of a 30% (w/v) iodixanol solution and centrifuged at 10,000 g at 4° C. Supernatants were discarded and the pellets were resuspended in 300 mL Rho GEF buffer (20 mM HEPES (pH 7.5), 150 mM NaCl, 5 mM $MgCl_2$, 1% (v/v) Triton X-100, 1 mM DTT with protease inhibitors). Suspensions were sonicated briefly, centrifuged at 14,000 g for 5 minutes at 4° C., and the remaining nuclear fraction supernatants were quantified for protein concentration via BCA assay. Subsequently, equal amounts of total GST fusion protein were incubated with fresh nuclear protein lysate (1 mg) for one hour, and precipitated lysates were resuspended in 2×SDS buffer containing protease inhibitors and resolved with SDS-PAGE.

Subsequently, equal amounts of total GST fusion protein were then incubated with nuclear protein lysate (1 mg), and precipitated lysates were resolved with SDS-PAGE.
Immunoprecipitation.

U87 cells were treated with 500 µM TMZ for the indicated times prior to lysis on ice in a buffer containing 10 mM Tris-HCl (pH 7.4), 0.5% Nonidet P-40, 150 mM NaCl, 1 mM phenylmethylsulfonyl fluoride, 1 mM EDTA, 2 mM sodium orthovanadate, 20 mM sodium fluoride, 10 µg/mL aprotinin, and 10 µg/mL leupeptin. Equivalent amounts of protein (1 mg) were pre-cleared and immunoprecipitated from the lysates using either SGEF or BRCA1 antibodies as indicated, or a control isotype-matched antibody, and then washed with lysis buffer followed by TX-100 buffer [10 mm HEPES (pH 7.4), 150 mm NaCl, 2 mm EDTA, 2 mm EGTA, 20 mm sodium fluoride, and 0.5% Triton X-100]. Samples were then re-suspended in 1×LDS sample buffer containing DTT and boiled, separated by SDS-PAGE, transferred to nitrocellulose for 1 h at 4° C., and then proteins were detected using SuperSignal West Dura Chemiluminescent Substrate (Thermo Fisher Scientific).
Small-Interfering RNA Transfection.

Small interfering RNA (siRNA) oligonucleotides specific for GL2 luciferase were described previously (19). BRCA1-specific siRNA target sequences are as follows: BRCA1-1 (5'-ACC ATA CAG CTT CAT AAA TAA-3' (SEQ ID NO:7)) and BRCA1-2 (5'-AAC CTA TCG GAA GAA GGC AAG-3'(SEQ ID NO:8)). Transient transfection of siRNA was performed using Lipofectamine RNAiMax. Cells were plated at 70% confluence in DMEM+10% FBS without antibiotics and were transfected within 8 h of plating. The siRNA and Lipofectamine were diluted separately in Opti-MEM (Thermo Fisher Scientific). After 5 min, the mixtures were combined and incubated for 20 min at room temperature to enable complex formation. siRNA oligonucleotides were transfected at 50 nM, and no cell toxicity was observed. Maximum inhibition of protein levels was achieved 48 to 72 h post-transfection.
Proliferation Studies.

Cell viability was determined via Alamar Blue. Briefly, glioma cells were plated in 96-well plates in quadruplicate for use as a standard curve of known cell counts, or plated in replicates of 8 at 3,000 cells per well to monitor proliferation over 72 h. After cell attachment of the standard curve, or 24 h post-attachment of experimental wells, cells were treated with 10% Alamar Blue (Trek Diagnostic Systems) for 5 h at 37° C. The absorbance was read at 560 nm and 595 nm and the cell viability was expressed as number of cells per well calculated relative to the standard curve for each line. Cell viability was repeatedly assessed daily over 72 h.
Immunofluorescence.

U87 control or shSGEF cells were plated onto 10-well glass slides, pre-coated with 10 µg/mL laminin. Twenty-four hours later, cells were treated with 500 µM TMZ for 48 h and fixed in 4% formaldehyde/PBS, permeabilized with 0.1% Triton X-100 dissolved in PBS, and incubated with antibodies to BRCA1 and phospho-H2A.X (Ser139). Slides were mounted with ProLong Gold Antifade Reagent with DAPI (Molecular Probes). Images were collected using a Zeiss LSM 510 microscope equipped with a 63× objective, ZEN 2009 image analysis software, and Adobe Photoshop CS3.
Gene Expression Analysis of SGEF and Fn14 Correlation.

Expression data generated using the Affymetrix U133 Plus 2.0 Array for 82 GB samples was downloaded from the REpository for Molecular BRAin Neoplasia DaTa (REMBRANDT) for correlation of ARHGEF26(SGEF) and TNFRSF12A (FN14) (20). The expression level of ARHGEF26 (SGEF) was calculated as the median of the three relative expression intensity values for the three probe sets annotated for ARHGEF26 (SGEF). There was a high correlation of all three ARHGEF26 (SGEF) probes sets to each other (Pearson correlation of 0.90 to 0.97). The relative expression intensity of the probe set 218368_s_at was used for TNFRSF12A (FN14) as it is the only probe set annotated for TNFRSF12A (FN14). The Pearson Product Moment Correlation was calculated using the R software code as supplied by (21).
Statistical Analysis.

Statistical analyses were done using the two-sample t test. $P<0.05$ was considered significant.

Results

TWEAK-Fn14 Signaling Induces SGEF mRNA and Protein Expression Via NF-κB.

It was previously reported that Fn14 signaling directs both pro-invasive and pro-survival responses in GB tumors via Rac1 and NF-κB, respectively (3, 4, 13). Also described was a role for the novel GEF, SGEF, in the promotion of Fn14-directed increased cell motility whereby Fn14 signaling enacted SGEF-required downstream RhoG and subsequently Rac1 activation (13). Of note, an analysis of 82 primary GB tumor specimens in the publicly available REMBRANDT dataset revealed a positive association between Fn14 and SGEF expression across the tissues (p<0.001) (FIG. 1A). It was previously shown that, similar to Fn14, SGEF expression was inversely correlated to patient survival among primary GB tumors (13). Thus, next was to determine whether SGEF played an additional role in pro-survival signaling within GB cells. Given that there is a positive correlation between SGEF and Fn14 expression, it was first analyzed whether Fn14 signaling played a role in the regulation of SGEF expression. Stimulation of T98G and U118 glioma cells with the TWEAK ligand resulted in increased SGEF mRNA and protein levels with increased levels apparent within two hours of treatment, indicating that SGEF expression is inducible under TWEAK-Fn14 regulation. (FIGS. 1B & C).

Figure 2:
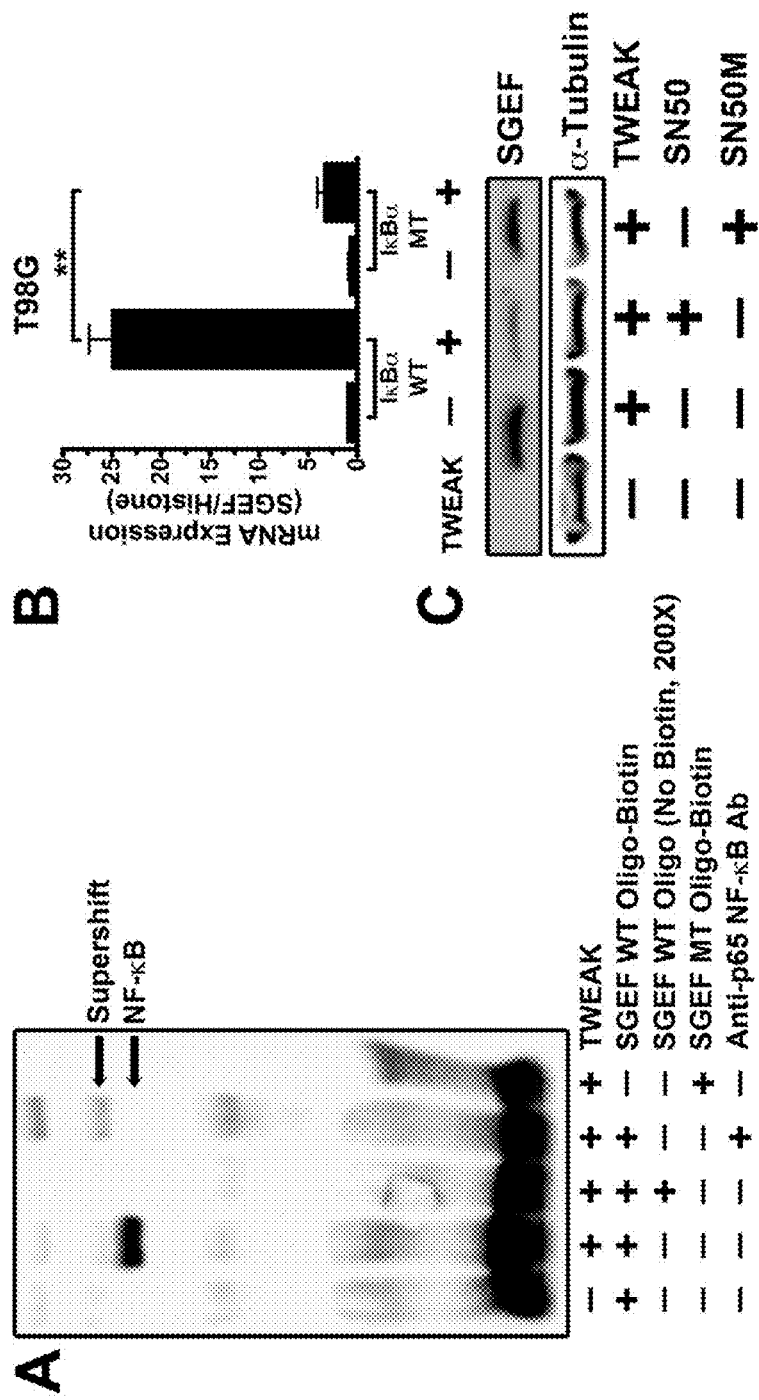
FIG. 2. NF-κB binds to the SGEF promoter region upon TWEAK stimulation and TWEAK-Fn14 induction of SGEF expression is dependent upon NF-κB activity. (A) T98G cells were treated with TWEAK (100 ng/mL). Nuclear proteins were isolated 2 hours post-treatment and incubated with biotin end-labeled, wild-type SGEF (SGEF wt) oligonucleotides containing the NF-κB consensus binding region. Proteins were also incubated with biotin end-labeled SGEF oligonucleotides containing mutated NF-κB consensus binding region (SGEF mt). In certain experiments, either 200-fold molar excess of unlabeled NF-κB-SGEF wt oligonucleotides or anti-p65 antibody was incubated with the nuclear lysates from TWEAK-treated cells. (B) T98G glioma cells were transiently transfected with either control or IκBαM super-repressor expressing plasmids for 24 hours, followed by serum starvation for an additional 16 hours (0.5% FBS DMEM), with subsequent TWEAK treatment in certain cases for 4 hours. Total RNA was isolated and SGEF mRNA expression was analyzed via qPCR with fold change relative to histone H3.3. (C) T98G glioma cells were cultured for 16 hours in reduced serum medium (0.5% FBS DMEM) followed by pre-treatment with SN50 NF-κB inhibitor or control non-inhibiting SN50M as indicated for 1 hour with the subsequent addition of TWEAK to all dishes for 4 hours. Protein lysates were resolved via SDS-PAGE and probed with the indicated antibodies.

Since NF-κB is an important promoter of cell survival in GB tumors (3, 4, 22), and Fn14 pro-survival signaling is dependent upon NF-κB up-regulation of pro-survival gene transcripts (3), it was next assessed whether the regulation of SGEF expression by TWEAK-Fn14 signaling required NF-κB. The SGEF promoter was analyzed, identifying the presence of an NF-κB p65 consensus sequence binding site at −2260 to −2238 base pairs upstream of the transcriptional start site including the 5' UTR. Using an electrophoretic mobility shift assay with wild-type and mutant NF-κB p65 consensus sequence oligonucleotides from the SGEF promoter region, it was assessed whether NF-κB binds to the SGEF promoter following treatment with TWEAK. SGEF wild-type but not mutant sequences shifted under nuclear lysate binding; the addition of an anti-p65 antibody confirmed the shift as p65 binding specific (FIG. 2A). To further determine whether TWEAK-Fn14 driven increase in SGEF expression is dependent upon NF-κB, T98G glioma cells were transiently transfected, either with plasmids expressing either control vector or IκBαM, an upstream super-repressor of NF-κB, or pharmacologically inhibited NF-kB activation via the cell permeable peptide inhibitor SN50 or control SN50M, and the SGEF mRNA or protein levels were analyzed following treatment with TWEAK. NF-κB inhibition either by IκBaM or SN50 resulted in diminished SGEF mRNA and protein expression, respectively, indicating that NF-κB is required for TWEAK-Fn14 induction of SGEF (FIGS. 2B & C).

Figure 3:
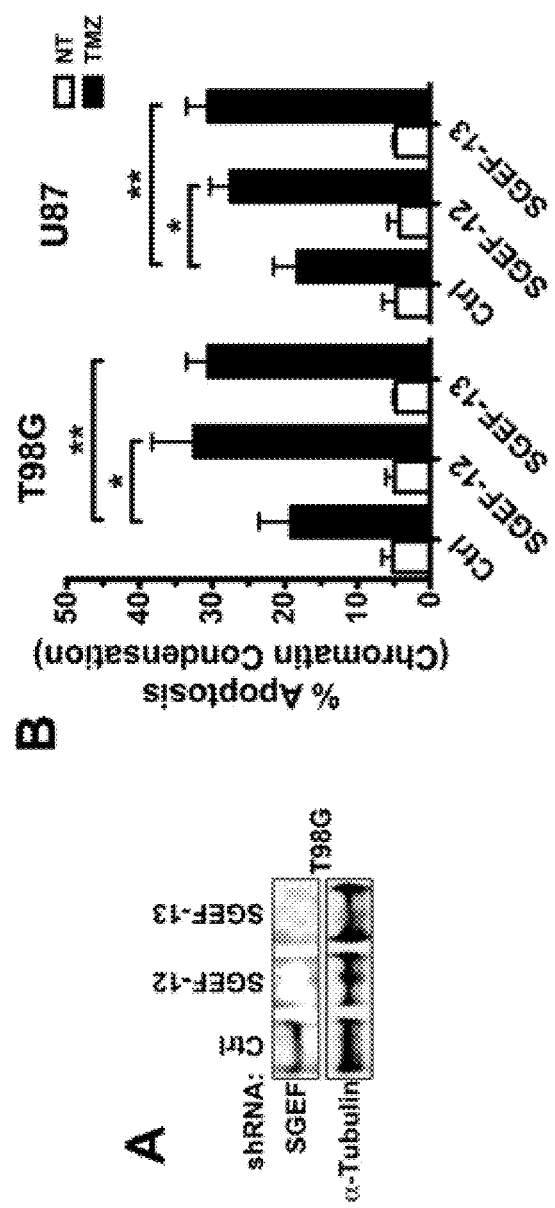
FIG. 3. Depletion of SGEF impairs colony formation following TMZ treatment and sensitizes glioma cells to TMZ-induced apoptosis. (A) Glioma cells were stably transduced with viruses expressing either control vector (Ctrl) or shRNA targeting SGEF (SGEF-12 & SGEF-13). (B & C) T98G and U87 glioma control cells (Ctrl) or shSGEF cells (SGEF-12 & SGEF-13) were treated for 48 hours with either control DMSO or TMZ (500 μM), and were either (B) plated onto 10-well slides pre-coated with 10 ug/mL laminin, stained for DAPI and counted for percent chromatin condensation, or (C) protein lysates were collected for immunoblotting with cleaved PARP. Data represent an average and SD of 3 replicates. (*$p<0.05$). (D) T98G, U87 and U118 control cells (Ctrl) or shSGEF cells were treated with either control DMSO or TMZ (500 μM) for 48 hours followed by plating at a density of 250 cells in triplicate for clonogenic studies. Observable colonies were recorded approximately one week following plating. Data represent an average and SD of 3 replicates. (*$p<0.01$).
Figure 3:
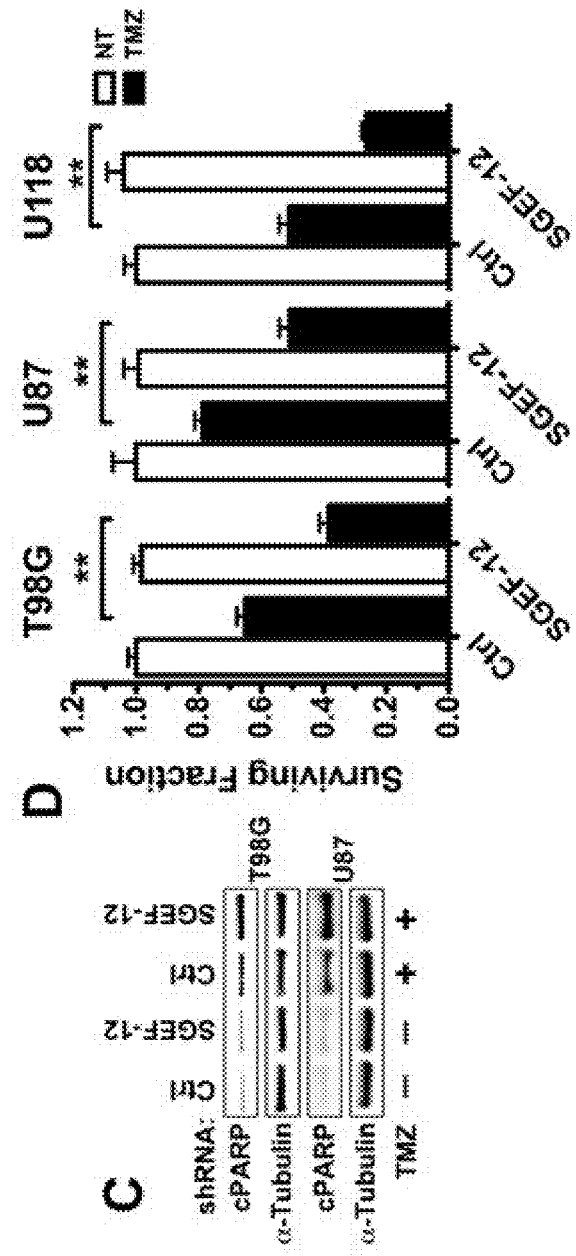

Depletion of SGEF impairs colony formation following TMZ treatment and sensitizes cells to TMZ-mediated apoptosis. Given SGEF expression is up-regulated by TWEAK-Fn14 in an NF-kB dependent fashion, it was assessed whether SGEF was important in pro-survival signaling in GB. To determine the importance of SGEF protein in response to TMZ, stable SGEF-depleted glioma cell lines were utilized, established via lentiviral-mediated transduction of either control (Ctrl) or shRNA targeting SGEF (SGEF-12 & SGEF-13) expressing vectors in T98G (FIG. 3A), U87 and U118 (previously published, (13)) glioma cell lines. Stable depletion of SGEF in T98G, U87 or U118 glioma cells does not alter proliferation (Data not shown). However, in T98G and U87 glioma cells with stable depletion of SGEF, treatment with TMZ for forty-eight hours followed by assessment for cellular apoptosis revealed that TMZ-treated SGEF-depleted glioma cells showed increased chromatin condensation (FIG. 3B) as well as elevated cleaved PARP on immunoblot analysis (FIG. 3C) in comparison to control TMZ treated cells. Therefore, the loss of SGEF protein increases TMZ-induced cytotoxicity. To further characterize the susceptibility of glioma cells with stable SGEF knockdown to TMZ, T98G, U87 and U118 glioma cells were treated for twenty-four hours with TMZ and colony growth formation was measured. Cells depleted of SGEF displayed significantly impaired colony formation after TMZ treatment as compared to control TMZ treated cells (FIG. 3D). The depletion of SGEF in un-treated glioma cells did not affect colony formation (FIG. 3D). Therefore, these data indicate that SGEF protein function is important in the recovery response following TMZ treatment.

Figure 4:
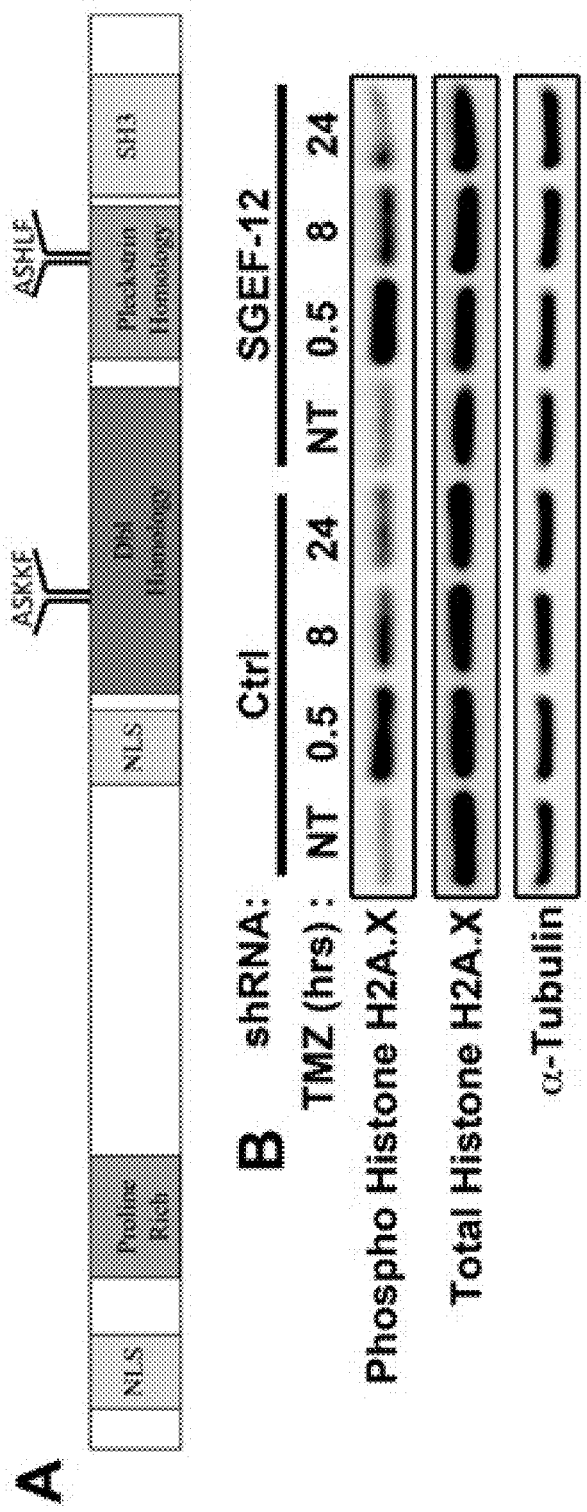
FIG. 4. TMZ induces nuclear SGEF activity and SGEF dependent BRCA1 activity, and promotes SGEF in complex with BRCA1. (A) A diagrammatic representation of the SGEF polypeptide sequence, containing two BRCT domains (ASKKF and ASHLF) at aa 493-497 and aa 741-745. (B) U87 control cells (Ctrl) or shSGEF cells (SGEF-12) were treated with TMZ (500 μM) for the indicated times, and protein lysates were analyzed by immunoblotting with phospho- and total-Histone H2A.X, as well as tubulin antibodies. (C) U87 glioma cells were treated with TMZ (500 μM) for the indicated times followed by isolation of nuclear proteins. SGEF activation in control and treated lysates was assessed using RhoG G15A-GST constructs with immunoblotting for antibodies as indicated. (D) U87 control cells (Ctrl) or shSGEF cells (SGEF-12) were treated with TMZ (500 μM) for the indicated times. Lysates were analyzed by immunoblotting with phospho- and total-BRCA1, as well as tubulin antibodies. (E & F) Immunoblot analysis of protein lysates, immunoprecipitated using either (E) SGEF- or (F) BRCA1-specific antibodies, from U87 cells treated with TMZ for the indicated times.
Figure 4:
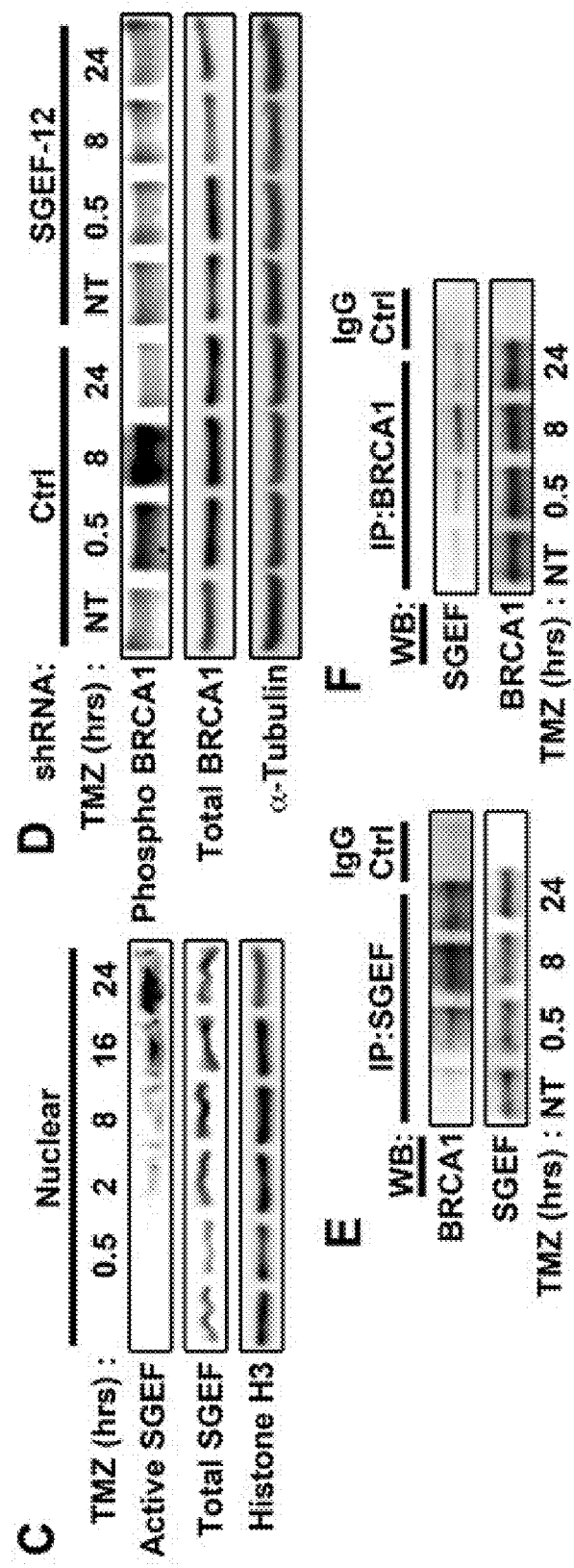

TMZ treatment induces nuclear SGEF activity and SGEF dependent BRCA1 activity, and promotes SGEF in complex with BRCA1. TMZ treatment is known to result in the formation of double strand DNA breaks (DSB) (9). The phosphorylation of histone (γH2A.X) is one of the earliest responses to DSB. γH2A.X is involved in the recruitment of and localization of DNA repair proteins and thus this phosphorylation is indicative of DNA damage DSB foci (23). SGEF contains two nuclear localization sequences (FIG. 4A) (24) and has previously been shown to be capable of nuclear localization, although the role of nuclear SGEF has not been described (25). U87 glioma cells were analyzed over twenty-four hours of treatment with TMZ and H2A.X phosphorylation levels were assessed in control or SGEF depleted lines (FIG. 4B). The phosphorylation of H2A.X occurred rapidly within 30 minutes of TMZ treatment in either control or SGEF depleted conditions, thus indicating that SGEF does not play a role in preventing the formation of DNA damage foci subsequent to TMZ treatment.

While SGEF depletion does not hinder TMZ-induced DNA damage, it was assessed whether SGEF plays a role in the coordinated response to DNA damage. It was first assessed whether the activity of SGEF is altered following TMZ treatment. U87 glioma cells treated for twenty-four hours with TMZ were fractionated for nuclear lysates, in which SGEF activity was determined using RhoG G15A nucleotide free mutant constructs (17). The results indicated that treatment with TMZ resulted in increased SGEF activity in the nucleus (FIG. 4C), further supporting a role for SGEF in the response to TMZ treatment. Use of functional site prediction analysis suggests that SGEF contains two phosphopeptide domain motifs at amino acids 493-497 (ASKKF) and 741-745 (ASHLF) (FIG. 4A) which can directly interact with the BRCT (carboxy-terminal) domain of BRCA1. BRCT domains are present in several DNA damage response proteins (26), and the phosphorylation of BRCA1 occurs rapidly in response to DNA damaging agents (10). Therefore, it was sought to determine whether SGEF is important in BRCA1 activation following TMZ treatment. U87 glioma cells were treated for twenty-four hours with TMZ and the phosphorylation of BRCA1 was assessed between control and SGEF depleted lines (FIG. 4D). The depletion of SGEF prevented TMZ-induced BRCA1 phosphorylation. It was then assessed whether treatment with TMZ induces complex formation between SGEF and BRCA1. U87 glioma cells treated for twenty-four hours with TMZ were analyzed via immunoprecipitation of SGEF and BRCA1. Minimal SGEF and BRCA1 co-immunoprecipitated from lysates of untreated cells, however TMZ treatment induced rapid complex formation between SGEF and BRCA1 within thirty minutes, which was sustained over the twenty-four hour time-course (FIGS. 4E & F). Thus SGEF may function in part to promote the BRCA1 response to DNA damage.

Figure 5:
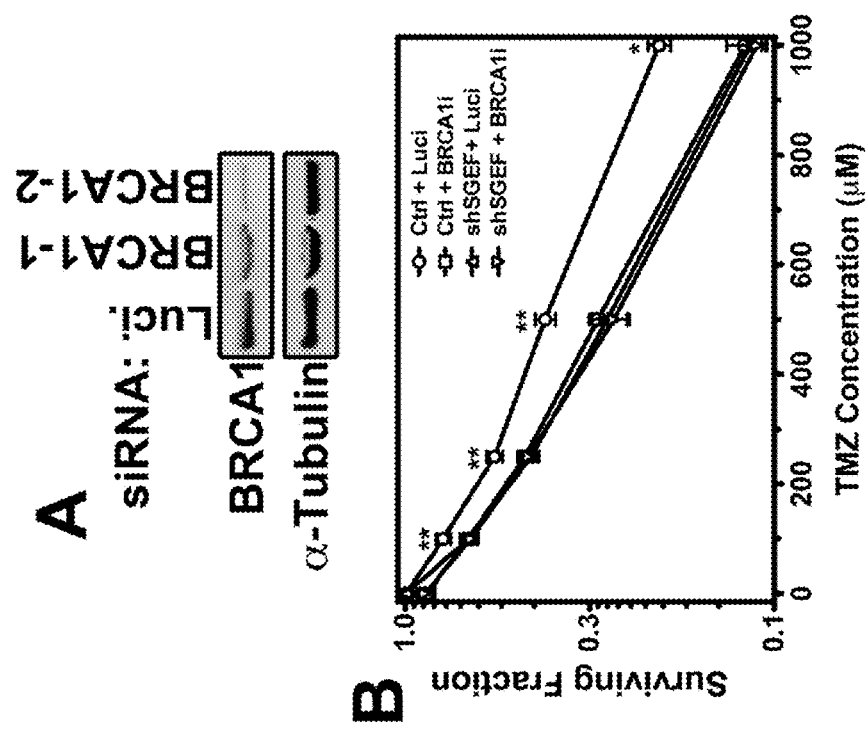
FIG. 5. Depletion of BRCA1 impairs colony formation following TMZ treatment and is not enhanced by concurrent depletion of SGEF. (A) U87 cells were treated with siRNA targeting either firefly luciferase as a control (Luci) or BRCA1 (BRCA1-1 & BRCA1-2) at 20 nM or 50 nM concentrations. Protein knockdown was confirmed via immunoblot analysis for BRCA1. (B) Colony formation capacity of parental U87 cells and U87 shSGEF cells was evaluated after transfection with siRNA for either luciferase or BRCA1 (BRCA1-2) at 50 nM and treatment at varying concentrations with TMZ. Cells were plated at a density of 250 cells in triplicate for clonogenic studies. Observable colonies were recorded approximately one week following plating. Data reported as the surviving fraction represent an average and SD of 3 replicates. (*$p<0.01$).

Depletion of BRCA1 impairs colony formation following TMZ treatment, which is not enhanced by concomitant SGEF depletion. Depletion of SGEF impairs cell survival following TMZ treatment (FIG. 3D). To assess whether SGEF may promote a divergent response to TMZ treatment in addition to the promotion of a BRCA1-mediated response, BRCA1 was depleted via transient siRNA transfection (FIG. 5A) in control glioma cells or glioma cells stably depleted of SGEF and treated the cells with TMZ. Depletion of BRCA1 impaired survival to TMZ treatment similar to that observed after SGEF depletion alone. The combination of BRCA1 depletion in SGEF depleted cells did not result in any significant further impaired cell survival following TMZ treatment (FIG. 5B). Given that there is no additive or synergistic effect of the dual shutdown, these data support that SGEF works along the same pathway in concert with BRCA1 in the DNA damage repair response.

Discussion

Embodiments of the invention generally related to the relationship between SGEF and in both therapeutic resistance and cell survival contexts. SGEF protein expression is induced in glioma cells under TWEAK-Fn14 signaling dependent upon NF-κB. NF-κB signaling has been well characterized to promote both GB cell invasion and survival (3, 4, 22, 27), and elevated or constitutive NF-κB activity has been demonstrated in gliomas and correlates with increasing brain tumor grade (27, 28). NF-κB signaling has specifically been shown to protect cells against the standard of care treatments in GB. The inhibition of IκBα phosphorylation prevents NF-κB activity and sensitizes glioma cells to radiation treatment (29) and NF-κB is an important player in promoting resistance to 06-alkylation (30), a TMZ induced DNA damage modification.

TWEAK-Fn14 signaling is one notable pathway in glioma that utilizes Rac1 dependent NF-κB activation to promote cell invasion and cytotoxic therapy resistance with enhanced cell survival (3, 4, 31). To date, SGEF has been largely associated with a role in promoting cell motility; SGEF has been shown to promote the invasive capacity of HPV transformed tumor cells and actin cytoskeleton remodeling after *salmonella* infection (25, 32). In GB tumors, in addition to a role in the promotion of cell invasion, it has been previously described that SGEF is significantly overexpressed and is correlated with poor patient outcome (13). Here reported is the role of SGEF in promoting cell survival. It was shown that TWEAK binding to Fn14 fosters NF-κB promoter occupancy of SGEF in glioblastoma, and that the TWEAK-Fn14 up-regulation of SGEF mRNA and protein expression is dependent upon NF-κB function. The link between Fn14 and SGEF in GB is further supported on the basis of mRNA expression analysis indicating a strong positive correlation in expression of the two genes among a panel of primary tumor specimens in the publicly available REMBRANDT dataset of 82 GB tumors (FIG. 1A). Of note, this correlation was not significant when brain tumors of all grades were considered (data not shown) but was highly statistically significant within GB tumors alone, indicating the relationship between SGEF and Fn14 may be specific to malignant progression.

Figure 6:
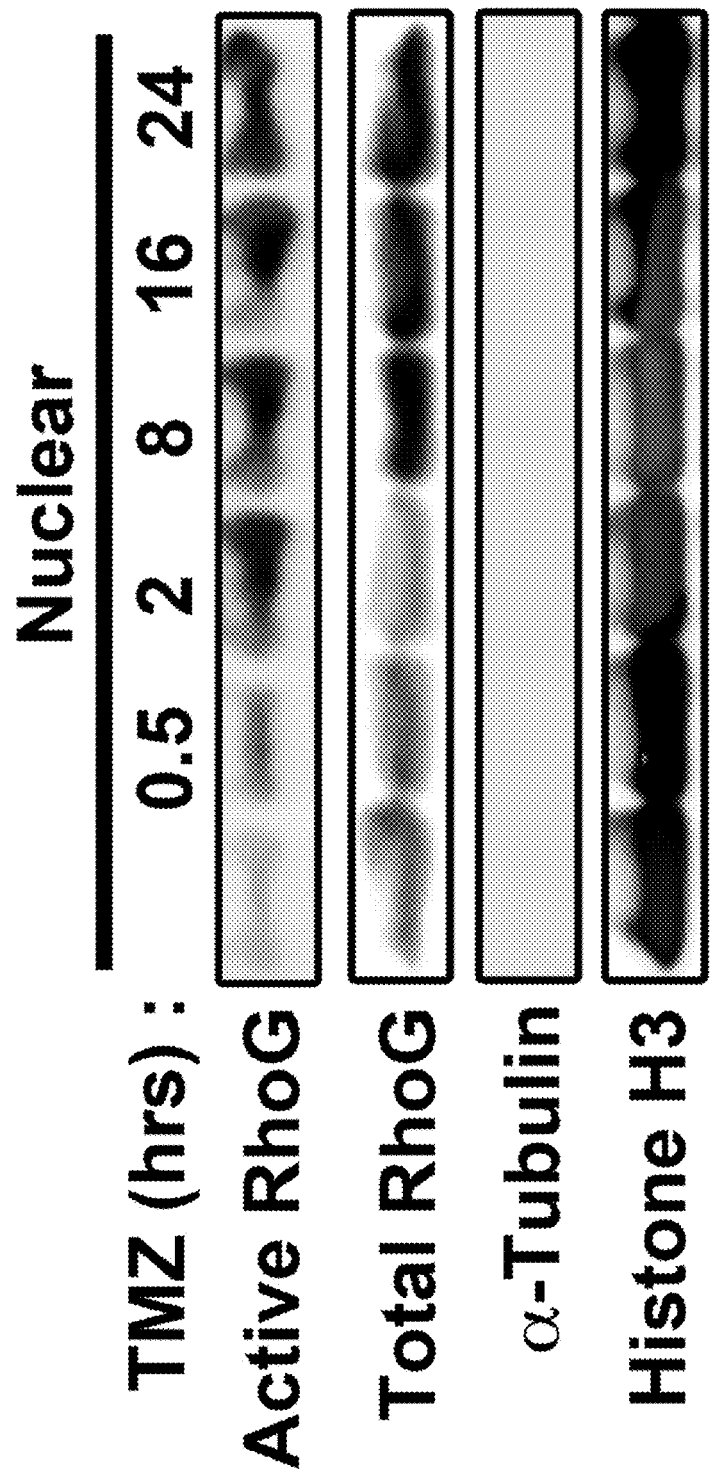
FIG. 6. TMZ treatment induces nuclear RhoG activity. U87 glioma cells were treated with TMZ (500 μM) for the indicated times followed by isolation of nuclear proteins. RhoG activation in control and treated lysates was assessed using a GST-tagged ELMO construct. Unpurified lysate was immunoblotted for RhoG as a loading control, as well as for tubulin and histone H3 for cytoplasmic and nuclear fractionation controls, respectively.

The data suggest an important role for SGEF in the response of glioma cells to TMZ treatment. It was shown that the shRNA-mediated depletion of SGEF does not affect cell proliferation (Data not shown), but does impair the ability of glioma cells to form colonies following TMZ treatment and leads to glioma cell sensitization to TMZ-induced cell death via apoptosis. SGEF is known to contain two nuclear localization sequences (24), and has been reported to localize in the nucleus of cells (25). The data shows that TMZ treatment of glioma cells induces nuclear activity of SGEF in a time-dependent fashion. Moreover, SGEF is known to facilitate guanine nucleotide exchange for the GTPase RhoG (33) and RhoG has been shown to contain a nuclear localization sequence (34), the significance of which remains unknown to date. The data indicate that RhoG becomes active in the nucleus, similar to SGEF, in response to TMZ treatment of glioma cells (FIG. 6). Therefore, nuclear RhoG may play a role in the SGEF pro-survival response to TMZ treatment.

Figure 7:
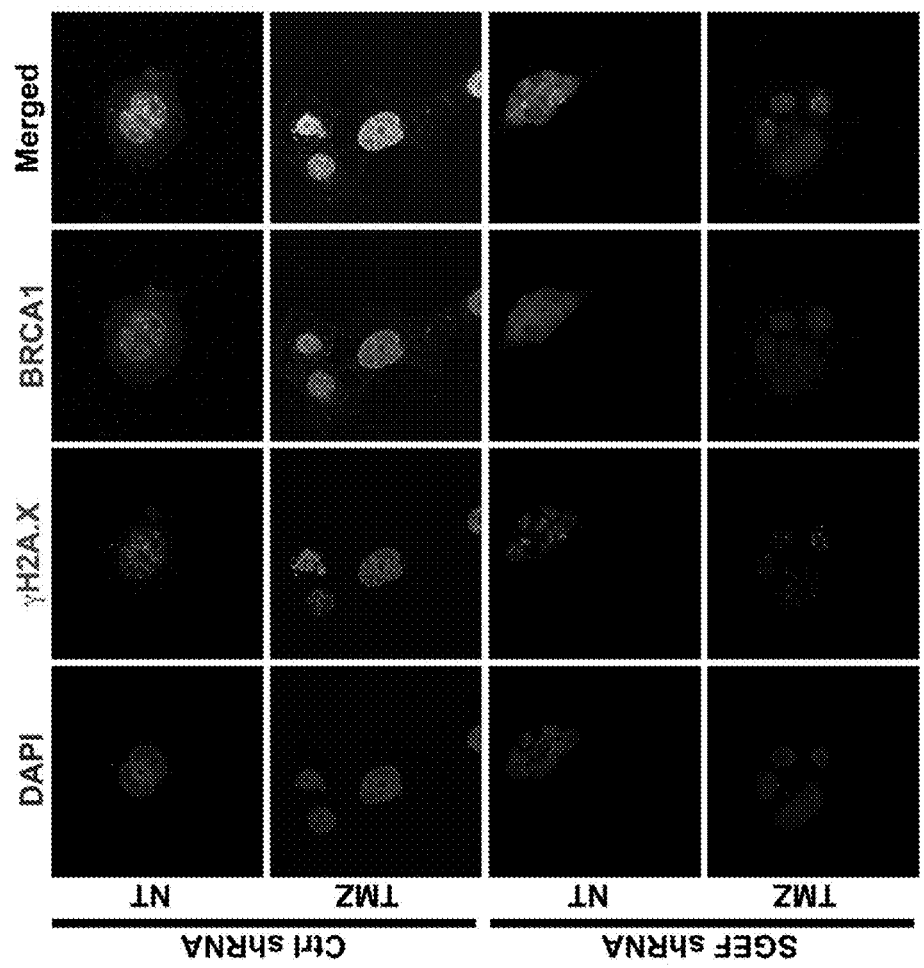
FIG. 7. SGEF is required for BRCA1 recruitment to H2A.X foci following TMZ treatment. U87 control or shSGEF cells were treated for 48 hours with either control DMSO or TMZ (500 μM) and plated onto 10-well slides pre-coated with 10 ug/mL laminin. Cells were stained for DAPI, H2A.X, and BRCA1, and images were obtained for immunofluorescence.
Figure 8:
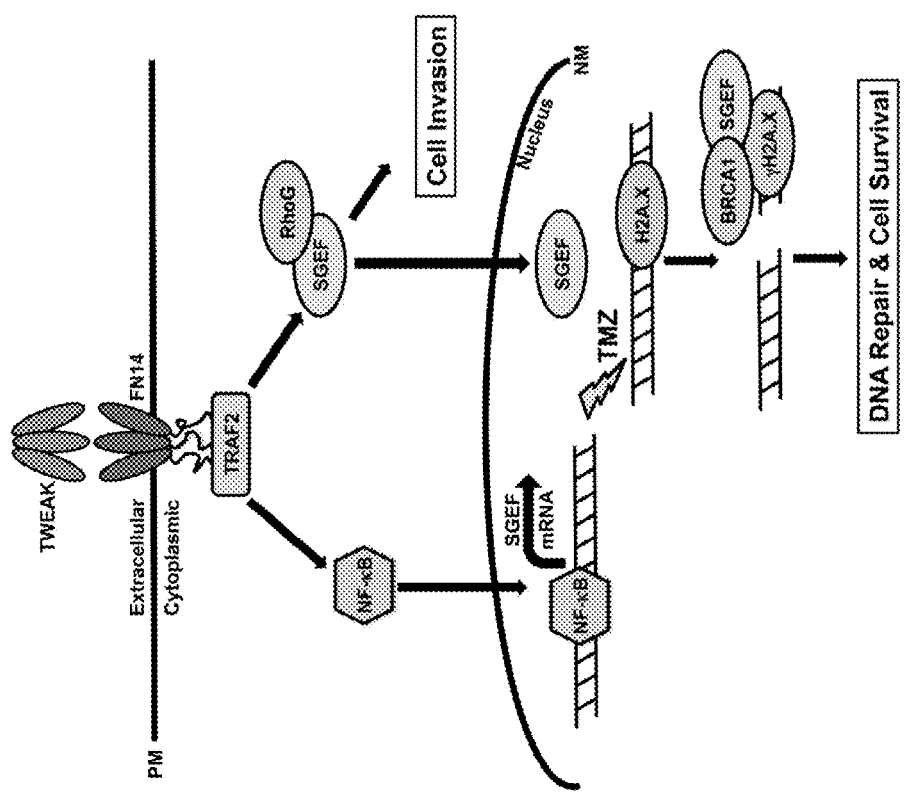
FIG. 8. Schematic model of Fn14-NF-κB-dependent up-regulation of SGEF expression and SGEF pro-survival response to TMZ treatment. TWEAK interaction with the Fn14 receptor leads to the NF-κB mediated up-regulation of SGEF mRNA and protein expression. SGEF protein promotes glioma cell survival and is associated with TMZ resistance and DNA repair pathway activation via complex with BRCA1.

Sequence analysis of SGEF revealed two BRCT binding domains with the potential for binding BRCA1. It has been demonstrated that SGEF is found in complex with BRCA1 following TMZ treatment, and that phosphorylation of BRCA1 is dependent upon SGEF. Thus, the decreased capacity of TMZ-induced BRCA1 phosphorylation in SGEF depleted glioma cells may help explain the observed significantly impaired capacity of glioma cells to recover colony formation and the increased apoptosis in TMZ-treated SGEF-depleted glioma cells. Moreover, while it was shown that the formation of DNA damage foci marked by H2A.X phosphorylation following TMZ addition is independent of SGEF function, the data indicate that SGEF is required for BRCA1 recruitment to H2A.X foci following TMZ treatment (FIG. 7). The determination of the specific functional site responsible for SGEF interaction with BRCA1 will be the focus of future studies. Proposed was a scheme of TWEAK-Fn14 inducible SGEF mRNA and protein expression dependent upon NF-κB nuclear translocation and activity, whereby increased SGEF levels promote a pro-survival phenotype in the face of TMZ treatment by promotion of BRCA1 DNA damage response activity (FIG. 8).

BRCA1 has been shown to transiently interact at sites of damage or stalled replication forks with the role of homologous recombination. BRCA1 also functions in NHEJ, and S- and G2-M-phase checkpoints, however some reports suggest that BRCA1 preferentially promotes the error free HR pathway for DNA repair over NHEJ to preserve chromosome stability (10). Cancers known to have a deficiency of the HR repair proteins BRCA1 and BRCA2 display particular sensitivity to poly(ADP)-ribose polymerase (PARP) inhibition, a protein whose activity normally facilitates single strand damage repair. When unrepaired, these single strands are converted to double strand breaks during replication, which are then unable to be corrected due to a non-functioning HR system (35). Interestingly in gliomas, the inhibition of HR via siRNA-mediated depletion of Rad51 or BRCA2 greatly sensitized glioma cells to TMZ, the effect of which was enhanced by concurrent PARP inhibition (36). These studies further support the notion that targeting the modulation of BRCA1 activity as regulated by SGEF expression may enhance cell killing in GB tumors, and future studies will address the potential for synergistic lethality in targeting this axis in combination with other inhibitors of DNA repair.

Figure 9:
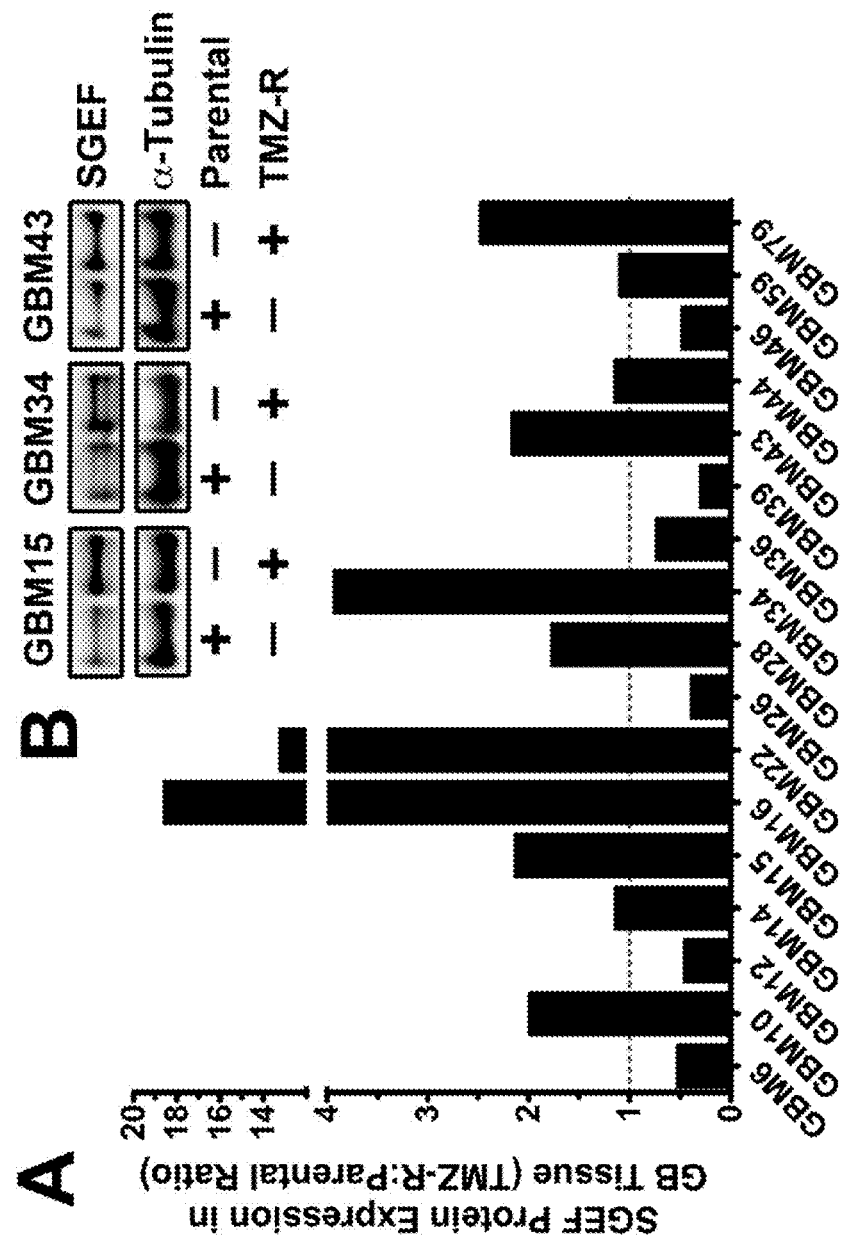
FIG. 9. SGEF protein levels across a panel of primary parental versus TMZ-R xenografts. (A) SGEF protein levels from 17 pooled xenograft samples comparing parental tumor versus each corresponding tumor derivative selected in vivo for TMZ resistance (TMZ-R), and plotted after densitometry normalized to tubulin control. (B) Inset contains three xenograft representative western blot images.

Tumor modulation of DNA repair pathways has been described as one main avenue of glioblastoma resistance to TMZ. Gene expression associated with promoter hypomethylation of the DNA repair protein 06-methylguanine-DNA methyltransferase (MGMT) allows for notable inherent tumor resistance in glioblastomas. However epigenetic silencing of MGMT by promoter hypermethylation has been shown to occur in 30-60% of glioblastoma tumors, and it has been suggested that MGMT-deficient GB cells may be particularly susceptible to targeting HR in combination with additional DNA repair proteins including PARP inhibition (35). In addition, acquired TMZ resistance has been demonstrated by silencing of DNA mismatch repair genes through treatment-induced mutations which then allows the tumor cell to escape a futile repair process otherwise leading to cell death, while the epigenetic silencing of DNA base excision repair genes may predict TMZ sensitivity (35). Given the role of DNA repair pathways in the tumor cell response to TMZ treatment, SGEF expression was further characterized in the setting of TMZ chemoresistance using a panel of primary GB xenografts treated in vivo with TMZ to derive matched parental and TMZ-resistant (TMZ-R) pairs (37). Interestingly, protein expression of SGEF was found to be higher in the resistant lines versus the parental in a subset (8/17) of samples (FIG. 9), suggesting in some GB tumors increased SGEF expression may result following exposure to TMZ. It is unknown whether the high expression of SGEF in these primary tumors directly confers resistance to TMZ, however the study of these lines is currently under investigation. Moreover, it is unknown why SGEF protein expression is elevated in only a subset of the TMZ-R GB xenografts. It is possible that genetic heterogeneity of the patient-derived parental and TMZ-resistant lines may play a role in perceived SGEF expression due to sampling bias, and this concern will also be addressed in future studies.

Interestingly, radial migration analysis of GBM14 and GBM14 TMZ-R primary xenografts revealed an elevated rate of cell migration corresponding to the TMZ-R setting (data not shown). SGEF promotes cell migration and invasion in glioblastoma via activation of the Rho GTPase RhoG with subsequent RhoG-dependent activation of Rac1 and the formation of lamellipodia (13). Thus, NF-κB mediated increased SGEF expression may be one mechanism that facilitates the increased cell motility of TMZ-R glioma cells. Indeed, increased invasive capacity has been previously reported in glioma as a response to cytotoxic therapy. For example, it has been shown that radiation of glioblastoma leads to the enhanced cell invasive potential via activation of the Rho-PI-3K signaling pathway (38). In addition, the pro-invasive integrins, αvβ3 and αvβ5, have been demonstrated to mediate a pro-survival response in glioma to radiation through integrin-linked kinase and the RhoB GTPase (39), thus implying overlapping roles for mediators of cell motility with the promotion of cell survival. Of note, there have also been multiple reports of increased cell invasiveness resulting from treatment with chemotherapeutic agents among several tumor types (40-42). Thus, the roles of invasion and survival are interconnected in the promotion of disease progression, and there is mounting evidence for overlap between these two processes (43). SGEF therefore presents a novel hub in the interrelated axes of tumor cell invasion and survival.

Despite advances in medical technology and treatment, GB prognosis has remained largely unchanged over the last several decades (44, 45). The ability of glioma cells to survive undeterred from current treatment strategies implies that new therapeutic avenues are necessary for treatment of this disease. There is accumulating evidence that combinatorial therapy that includes use of treatment modalities designed to hamper the DNA repair mechanisms of the cell may provide a significant added survival benefit to patients over the standard of care alone or when used in combination with inhibitors of other GB deregulated pathways (46-49). Moreover therapy aimed at mediators of invasion can also lead to increased chemotherapeutic sensitivity (5, 6). Thus, pathways deregulated in GB that promote both TMZ resistance and cell motility represent novel therapeutic targets in future drug design. Our data support a role for SGEF in both the promotion of cell invasion and cell survival signaling within GB tumors and provide a rationale for targeting this signaling axis. Interestingly, there has been a recent report of the RhoJ GTPase in promoting melanoma chemoresistance by suppressing DNA damage sensing pathways including the uncoupling of ATR from its downstream effectors with resulting decreased DNA damage-induced apoptosis (50). Thus the role of GEFs and GTPases in chemoresistance via modulation of DNA repair mechanisms is an emerging field in which this invention has validated a role for SGEF in GB.

REFERENCES

So as to reduce the complexity and length of the Detailed Specification, Inventors herein expressly incorporate by reference to the extent applicable, all of the following materials.
1. Hoelzinger D B, Mariani L, Weis J, Woyke T, Berens T J, McDonough W S, et al. Gene expression profile of glioblastoma multiforme invasive phenotype points to new therapeutic targets. Neoplasia. 2005; 7:7-16.
2. Mariani L, Beaudry C, McDonough W S, Hoelzinger D B, Demuth T, Ross K R, et al. Glioma cell motility is associated with reduced transcription of proapoptotic and proliferation genes: a cDNA microarray analysis. J Neurooncol. 2001; 53:161-76.
3. Tran N L, McDonough W S, Savitch B A, Sawyer T F, Winkles J A, Berens M E. The tumor necrosis factor-like weak inducer of apoptosis (TWEAK)-fibroblast growth factor-inducible 14 (Fn14) signaling system regulates glioma cell survival via NFkappaB pathway activation and BCL-XL/BCL-W expression. J Biol Chem. 2005; 280:3483-92.
4. Tran N L, McDonough W S, Savitch B A, Fortin S P, Winkles J A, Symons M, et al. Increased fibroblast growth factor-inducible 14 expression levels promote glioma cell invasion via Rac1 and nuclear factor-kappaB and correlate with poor patient outcome. Cancer Res. 2006; 66:9535-42.
5. Munson J M, Fried L, Rowson S A, Bonner M Y, Karumbaiah L, Diaz B, et al. Anti-invasive adjuvant therapy with imipramine blue enhances chemotherapeutic efficacy against glioma. Sci Transl Med. 2012; 4:127ra36.
6. Acharyya S, Oskarsson T, Vanharanta S, Malladi S, Kim J, Morris P G, et al. A CXCL1 Paracrine Network Links Cancer Chemoresistance and Metastasis. Cell. 2012; 150: 165-78.
7. Han S, Li Z, Master L M, Master Z W, Wu A. Exogenous IGFBP-2 promotes proliferation, invasion, and chemoresistance to temozolomide in glioma cells via the integrin beta1-ERK pathway. British journal of cancer. 2014; 111:1400-9.
8. Hanahan D, Weinberg R A. Hallmarks of cancer: the next generation. Cell. 2011; 144:646-74.
9. Roos W P, Kaina B. DNA damage-induced apoptosis: From specific DNA lesions to the DNA damage response and apoptosis. Cancer letters. 2012.
10. Zhang J, Powell S N. The role of the BRCA1 tumor suppressor in DNA double-strand break repair. Molecular cancer research: MCR. 2005; 3:531-9.
11. Lukas J, Lukas C, Bartek J. More than just a focus: The chromatin response to DNA damage and its role in genome integrity maintenance. Nature cell biology. 2011; 13:1161-9.
12. Fortin S P, Ennis M J, Savitch B A, Carpentieri D, McDonough W S, Winkles J A, et al. Tumor necrosis factor-like weak inducer of apoptosis stimulation of glioma cell survival is dependent on Akt2 function. Mol Cancer Res. 2009; 7:1871-81.
13. Fortin Ensign S P, Mathews I T, Eschbacher J M, Loftus J C, Symons M H, Tran N L. The Src homology 3 domain-containing guanine nucleotide exchange factor is overexpressed in high-grade gliomas and promotes tumor necrosis factor-like weak inducer of apoptosis-fibroblast growth factor-inducible 14-induced cell migration and 14. Tran N L, McDonough W S, Donohue P J, Winkles J A, Berens T J, Ross K R, et al. The human Fn14 receptor gene is up-regulated in migrating glioma cells in vitro and overexpressed in advanced glial tumors. Am J Pathol. 2003; 162:1313-21.
15. Franken N A, Rodermond H M, Stap J, Haveman J, van Bree C. Clonogenic assay of cells in vitro. Nat Protoc. 2006; 1:2315-9.
16. Kwiatkowska A, Didier S, Fortin S, Chuang Y, White T, Berens M E, et al. The small GTPase RhoG mediates glioblastoma cell invasion. Molecular cancer. 2012; 11:65.
17. Garcia-Mata R, Wennerberg K, Arthur W T, Noren N K, Ellerbroek S M, Burridge K. Analysis of activated GAPs and GEFs in cell lysates. Methods in Enzymology. 2006; 406:425-37.
18. Guilluy C, Dubash A D, Garcia-Mata R. Analysis of RhoA and Rho GEF activity in whole cells and the cell nucleus. Nature protocols. 2011; 6:2050-60.
19. Salhia B, Tran N L, Chan A, Wolf A, Nakada M, Rutka F, et al. The guanine nucleotide exchange factors trio, Ect2, and Vav3 mediate the invasive behavior of glioblastoma. The American journal of pathology. 2008; 173:1828-38.
20. REpository for Molecular BRAin Neoplasia DaTa (REMBRANDT) database (National Cancer Institute. 2005. REMBRANDT home page. http://rembrandt.nci.nih.gov. Accessed 2012 Nov. 26).
21. Wessa P., (2012) Pearson Correlation (v1.0.6) in Free Statistics Software (v1.1.23-r7), Office for Research Development and Education, URL http://www.wessa.net/rwasp_correlation.wasp/.
22. Robe P A, Bentires-Alj M, Bonif M, Rogister B, Deprez M, Haddada H, et al. In vitro and in vivo activity of the nuclear factor-kappaB inhibitor sulfasalazine in human glioblastomas. Clin Cancer Res. 2004; 10:5595-603.
23. Kuo L J, Yang L X. Gamma-H2AX—a novel biomarker for DNA double-strand breaks. In Vivo. 2008; 22:305-9.
24. Qi H, Fournier A, Grenier J, Fillion C, Labrie Y, Labrie C. Isolation of the novel human guanine nucleotide exchange factor Src homology 3 domain-containing guanine nucleotide exchange factor (SGEF) and of C-terminal SGEF, an N-terminally truncated form of SGEF, the expression of which is regulated by androgen in prostate cancer cells. Endocrinology. 2003; 144:1742-52.
25. Krishna Subbaiah V, Massimi P, Boon S S, Myers M P, Sharek L, Garcia-Mata R, et al. The invasive capacity of HPV transformed cells requires the hDlg-dependent enhancement of SGEF/RhoG activity. PLoS Pathog. 2012; 8:e1002543.
26. Gerloff D L, Woods N T, Farago A A, Monteiro A N. BRCT domains: A little more than kin, and less than kind. FEBS Lett. 2012; 586:2711-6.
27. Raychaudhuri B, Han Y, Lu T, Vogelbaum M A. Aberrant constitutive activation of nuclear factor kappaB in glioblastoma multiforme drives invasive phenotype. Journal of neuro-oncology. 2007; 85:39-47.
28. Conti A, Ageunnouz M, La Torre D, Cardali S, Angileri F F, Buemi C, et al. Expression of the tumor necrosis factor receptor-associated factors 1 and 2 and regulation of the nuclear factor-kappaB antiapoptotic activity in human gliomas. Journal of neurosurgery. 2005; 103:873-81.
29. Ding G R, Honda N, Nakahara T, Tian F, Yoshida M, Hirose H, et al. Radiosensitization by inhibition of IkappaB-alpha phosphorylation in human glioma cells. Radiat Res. 2003; 160:232-7.
30. Bredel M, Bredel C, Juric D, Duran G E, Yu R X, Harsh G R, et al. Tumor necrosis factor-alpha-induced protein 3 as a putative regulator of nuclear factor-kappaB-mediated resistance to O6-alkylating agents in human glioblastomas. Journal of clinical oncology: official journal of the American Society of Clinical Oncology. 2006; 24:274-87.
31. Brown S A, Richards C M, Hanscom H N, Feng S L, Winkles J A. The Fn14 cytoplasmic tail binds tumour-necrosis-factor-receptor-associated factors 1, 2, 3 and 5 and mediates nuclear factor-kappaB activation. Biochem J. 2003; 371:395-403.
32. Patel J C, Galan J E. Differential activation and function of Rho GTPases during *Salmonella*-host cell interactions. J Cell Biol. 2006; 175:453-63.
33. Ellerbroek S M, Wennerberg K, Arthur W T, Dunty J M, Bowman D R, DeMali K A, et al. SGEF, a RhoG guanine nucleotide exchange factor that stimulates macropinocytosis. Molecular biology of the cell. 2004; 15:3309-19.
34. Williams C L. The polybasic region of Ras and Rho family small GTPases: a regulator of protein interactions and membrane association and a site of nuclear localization signal sequences. Cellular signalling. 2003; 15:1071-80.
35. Johannessen T C, Bjerkvig R. Molecular mechanisms of temozolomide resistance in glioblastoma multiforme. Expert review of anticancer therapy. 2012; 12:635-42.
36. Quiros S, Roos W P, Kaina B. Rad51 and BRCA2—New molecular targets for sensitizing glioma cells to alkylating anticancer drugs. PloS one. 2011; 6:e27183.
37. Kitange G J, Mladek A C, Carlson B L, Schroeder M A, Pokorny J L, Cen L, et al. Inhibition of histone deacetylation potentiates the evolution of acquired temozolomide resistance linked to MGMT upregulation in glioblastoma xenografts. Clin Cancer Res. 2012; 18:4070-9.
38. Zhai G G, Malhotra R, Delaney M, Latham D, Nestler U, Zhang M, et al. Radiation enhances the invasive potential of primary glioblastoma cells via activation of the Rho signaling pathway. Journal of neuro-oncology. 2006; 76:227-37.
39. Monferran S, Skuli N, Delmas C, Favre G, Bonnet J, Cohen-Jonathan-Moyal E, et al. Alphavbeta3 and alphavbeta5 integrins control glioma cell response to ionising radiation through ILK and RhoB. International journal of cancer Journal international du cancer. 2008; 123:357-64.
40. Giavazzi R, Miller L, Hart I R. Metastatic behavior of an adriamycin-resistant murine tumor. Cancer research. 1983; 43:5081-6.
41. Liang Y, Meleady P, Cleary I, McDonnell S, Connolly L, Clynes M. Selection with melphalan or paclitaxel (Taxol) yields variants with different patterns of multidrug resistance, integrin expression and in vitro invasiveness. Eur J Cancer. 2001; 37:1041-52.
42. Glynn S A, Gammell P, Heenan M, O'Connor R, Liang Y, Keenan J, et al. A new superinvasive in vitro phenotype induced by selection of human breast carcinoma cells with the chemotherapeutic drugs paclitaxel and doxorubicin. British journal of cancer. 2004; 91:1800-7.
43. Alexander S, Friedl P. Cancer invasion and resistance: interconnected processes of disease progression and therapy failure. Trends Mol Med. 2012; 18:13-26.
44. Tait M J, Petrik V, Loosemore A, Bell B A, Papadopoulos M C. Survival of patients with glioblastoma multiforme has not improved between 1993 and 2004: analysis of 625 cases. Br J Neurosurg. 2007; 21:496-500.
45. Barnholtz-Sloan J S, Sloan A E, Schwartz A G. Relative survival rates and patterns of diagnosis analyzed by time period for individuals with primary malignant brain tumor, 1973-1997. Journal of neurosurgery. 2003; 99:458-66.
46. Barazzuol L, Jena R, Burnet N G, Meira L B, Jeynes J C, Kirkby K J, et al. Evaluation of poly (ADP-ribose) polymerase inhibitor ABT-888 combined with radiotherapy and temozolomide in glioblastoma. Radiat Oncol. 2013; 8:65.
47. McEllin B, Camacho C V, Mukherjee B, Hahm B, Tomimatsu N, Bachoo R M, et al. PTEN loss compromises homologous recombination repair in astrocytes: implications for glioblastoma therapy with temozolomide or poly(ADP-ribose) polymerase inhibitors. Cancer research. 2010; 70:5457-64.
48. Russo A L, Kwon H C, Burgan W E, Carter D, Beam K, Weizheng X, et al. In vitro and in vivo radiosensitization of glioblastoma cells by the poly (ADP-ribose) polymerase inhibitor E7016. Clin Cancer Res. 2009; 15:607-12.
49. Nadkarni A, Shrivastav M, Mladek A C, Schwingler P M, Grogan P T, Chen J, et al. ATM inhibitor KU-55933 increases the TMZ responsiveness of only inherently TMZ sensitive GBM cells. Journal of neuro-oncology. 2012; 110:349-57.
50. Ho H, Aruri J, Kapadia R, Mehr H, White M A, Ganesan A K. RhoJ regulates melanoma chemoresistance by suppressing pathways that sense DNA damage. Cancer research. 2012; 72:5516-28.

What is claimed is:

1. A method of sensitizing a patient with glioblastoma to a radiation therapy and/or chemotherapy, the method comprising the steps of:
administering to the patient with glioblastoma an src-homology 3 domain containing guanine nucleotide exchange factor (SGEF) inhibitor, wherein the SGEF inhibitor sensitizes the glioblastoma to the radiation therapy and/or chemotherapy, and wherein the SGEF inhibitor is a small hairpin RNA targeting the nucleic acid encoding for SGEF.

2. The method of claim 1, wherein the glioblastoma is invasive.

3. The method of claim 2, wherein the SGEF inhibitor converts the invasive glioblastoma to a non-migratory phenotype.

4. The method of claim 1, and further comprising administering a therapeutically effective amount of the radiation therapy and/or chemotherapy to the patient with glioblastoma.

5. The method of claim 4, wherein the radiation therapy and/or chemotherapy comprises the administration of one or more compounds selected from the group consisting of TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab.

6. A method of treating a patient with invasive glioblastoma, the method comprising the steps of:
a. sensitizing the patient with invasive glioblastoma by reducing an expression level of Src-homology 3 domain containing guanine nucleotide exchange factor (SGEF) using an SGEF inhibitor, wherein the SGEF inhibitor is a small hairpin RNA targeting the nucleic acid encoding for SGEF; and
b. administering a therapeutically effective amount of a radiation therapy and/or chemotherapy to the patient with invasive glioblastoma.

7. The method of claim 6, wherein the radiation therapy and/or chemotherapy comprises the administration of one or more compounds selected from the group consisting of TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab.

8. The method of claim 6, wherein the SGEF inhibitor converts the invasive glioblastoma to a non-migratory phenotype.

9. The method of claim 6, wherein the chemotherapy comprises administering a therapeutically effective amount of temozolomide.

10. The method of claim 6, wherein the radiation therapy comprises the administration of a therapeutically effective amount of radiation.

11. A method of treating a patient with glioblastoma, the method comprising the steps of:
a. sensitizing the patient with glioblastoma by reducing an expression level of Src-homology 3 domain containing guanine nucleotide exchange factor (SGEF) by administering to the patient a small hairpin RNA targeting SGEF; and b. administering a therapeutically effective amount of a radiation therapy and/or chemotherapy to the patient with glioblastoma.

12. The method of claim 11, wherein the radiation therapy and/or chemotherapy comprises the administration of one or more compounds selected from the group consisting of TROY inhibitors, Pyk2 inhibitors, Rac1 inhibitors, Dock180 inhibitors, Dock7 inhibitors, TWEAK inhibitors, Fn14 inhibitors, BAD inhibitors, and PI3k inhibitors, TRAIL, camptothecin, temozolomide and bevacizumab.

13. The method of claim 11, wherein the radiation therapy comprises the administration of a therapeutically effective amount of radiation.

* * * * *

UNITED STATES PATENT AND TRADEMARK OFFICE
CERTIFICATE OF CORRECTION

| | | |
|---|---|---|
| PATENT NO. | : 10,119,137 B2 | Page 1 of 1 |
| APPLICATION NO. | : 15/204969 | |
| DATED | : November 6, 2018 | |
| INVENTOR(S) | : Nhan Tran | |

It is certified that error appears in the above-identified patent and that said Letters Patent is hereby corrected as shown below:

In the Specification

Column 1, Line 11, before "BACKGROUND OF THE INVENTION" insert:
--STATEMENT REGARDING FEDERALLY SPONSORED RESEARCH
This invention was made with government support under grant number R01 CA130940 awarded by the National Institutes of Health. The government has certain rights in the invention.--

Signed and Sealed this
Eighteenth Day of April, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tgctgaaagg acaaggaaca                                                    20

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide

<400> SEQUENCE: 2
gtagttttga tacaggacag catt                                               24

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
ccactgaact tctgattcgc                                                    20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
gcgtgctagc tggatgtctt                                                    20

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide
```

```
<400> SEQUENCE: 5
gtctaggagg caaatcccag aaa                                          23

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide

<400> SEQUENCE: 6
gtctaggagc cagatcgcag aaa                                          23

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
accatacagc ttcataaata a                                            21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
aacctatcgg aagaaggcaa g                                            21
```